United States Patent [19]

Kim

[11] Patent Number: 5,380,719
[45] Date of Patent: Jan. 10, 1995

[54] QUINOXALINE BIPHENYL ANGIOTENSIN II INHIBITORS

[75] Inventor: Kyoung S. Kim, Lawrenceville, N.J.

[73] Assignee: E. R. Squibb & Sons, Inc., Princeton, N.J.

[21] Appl. No.: 876,729

[22] Filed: Apr. 28, 1992

[51] Int. Cl.$^6$ ............... A61K 31/675; A61K 31/495; C07D 403/10; C07D 403/12
[52] U.S. Cl. .................... 514/85; 514/234.8; 514/249; 544/116; 544/119; 544/230; 544/353; 544/354; 544/356; 548/252; 558/414; 558/415; 558/423; 560/19; 560/22; 560/103; 560/231
[58] Field of Search ............. 544/353, 354, 230, 116, 544/119; 514/249, 234.8, 85

[56] References Cited

U.S. PATENT DOCUMENTS

| | | | |
|---|---|---|---|
| 4,355,040 | 9/1982 | Furukawa et al. | 424/273 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 5,064,825 | 11/1991 | Chakravarty et al. | 514/221 |
| 5,066,660 | 11/1991 | Oxford et al. | 514/323 |

Primary Examiner—Emily Bernhardt
Attorney, Agent, or Firm—John M. Kilcoyne

[57] ABSTRACT

Angiotensin II inhibition is exhibited by

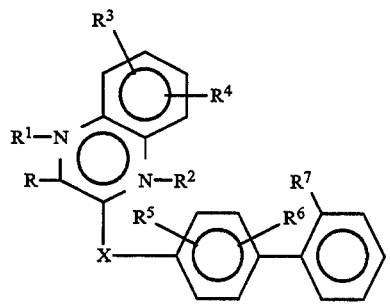

wherein:
X is —CH$_2$— or O;
R is hydrogen, alkyl, aryl, cycloalkyl, aralkyl, or cycloalkylalkyl;
R$^1$ and R$^2$ are each independently O or absent;
R$^3$ is hydrogen, alkyl, alkenyl, alkoxy, cycloalkyl, aryl, aralkyl, cycloalkylalkyl, halo, haloalkyl, or haloalkoxy;
R$^4$ is hydrogen, alkyl, alkenyl, alkoxy, aryl, cycloalkyl, aralkyl, cycloalkylalkyl, —R$^8$—OH, or —R$^8$-CO$_2$R$^9$;
and the remaining symbols are as defined in the specification.

15 Claims, No Drawings

QUINOXALINE BIPHENYL ANGIOTENSIN II INHIBITORS

FIELD OF THE INVENTION

This invention relates to novel quinoxalines that inhibit the action of angiotensin II, thus making them useful as antihypertensive agents.

BRIEF DESCRIPTION OF THE INVENTION

In accordance with the present invention, a compound of the formula

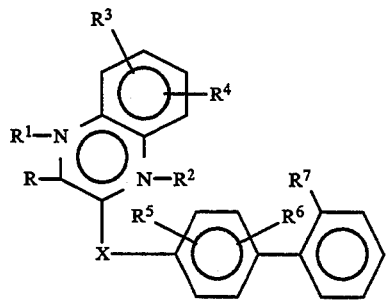

and pharmaceutically acceptable salts and prodrugs thereof inhibit the action of angiotensin II. In compound I and throughout this specification, the symbols are defined as follows:

X is —O— or —CH$_2$—;

R is hydrogen, alkyl, aryl, aralkyl, cycloalkyl, or cycloalkylalkyl;

R$^1$ and R$^2$ are each independently O or absent;

R$^3$ is hydrogen, alkyl, alkenyl, alkoxy, cycloalkyl, aryl, aralkyl, cycloalkylalkyl, —NR$^{17}$R$^{18}$, halo, haloalkyl (e.g., trifluoromethyl) or haloalkoxy;

R$^4$ is hydrogen, alkyl, alkenyl, alkoxy, aryl, cycloalkyl, aralkyl, cycloalkylalkyl, —R$^8$—OH, or —R$^8$-CO$_2$R$^9$;

R$^5$ and R$^6$ are each independently hydrogen, alkyl, alkoxy, halogen, or haloalkyl;

R$^7$ is —(CH$_2$)$_n$—CO$_2$R$^9$, 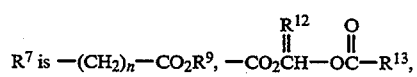

—NHSO$_2$haloalkyl

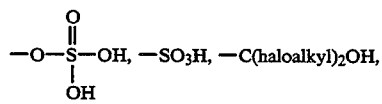

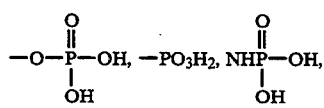

(optionally substituted with R$^9$), 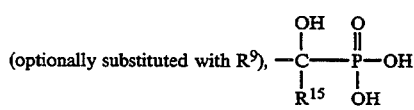

-continued

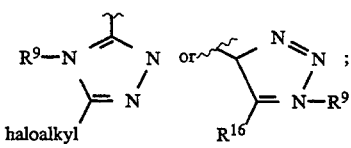

R$^8$ is a single bond, alkyl, alkenyl, aryl, or aralkyl;

R$^9$ is hydrogen, alkyl, cycloalkyl, aryl, aralkyl,

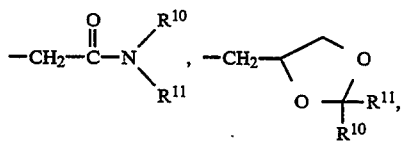

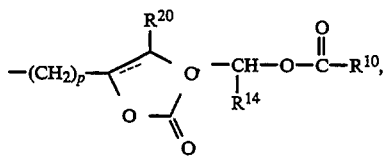

R$^{10}$ and R$^{11}$ are each independently hydrogen, alkyl, alkoxy, cycloalkyl, aryl, or aralkyl, or R$^{10}$ and R$^{11}$ together are —(CH$_2$)$_2$—, —(CH$_2$)$_3$—, —CH=CH—, or

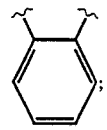

R$^{12}$ is hydrogen, alkyl, aryl, cycloalkyl, or aralkyl;

R$^{13}$ is alkyl, —NR$^{10}$R$^{11}$, or

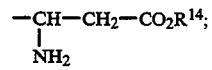

R$^{14}$ is hydrogen, alkyl, perfluoroalkyl, cycloalkyl, phenyl, or benzyl;

R$^{15}$ is hydrogen, alkyl, or phenyl;

R$^{16}$ is —CN, —NO$_2$, or —CO$_2$R$^{14}$;

R$^{17}$ and R$^{18}$ are each independently hydrogen, alkyl of 1 to 4 carbon atoms, phenyl, benzyl, α-methylbenzyl, or together with the nitrogen atom to which they are attached are

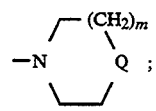

Q is —NR$^{19}$, —O—, or —CH$_2$—;

R$^{19}$ is hydrogen, alkyl, aryl, aralkyl, cycloalkyl, or cycloalkylalkyl;

R$^{20}$ is hydrogen, alkyl, aryl, cycloalkyl, aralkyl, or cycloalkylalkyl;

m is 0 or 1;

n is 0, 1, or 2; and p is 1, 2, 3, or 4.

For compound I, the following moieties are preferred:

X is —O—;

R is alkyl of 1 to 4 carbon atoms;
R² is O;
R³ is hydrogen, alkoxy, or haloalkoxy;
R⁴ is hydrogen or —CO₂R⁹;
R⁵ and R⁶ are hydrogen;
R⁷ is -5-tetrazolyl; and
R⁹ is hydrogen, alkyl, alkali metal,

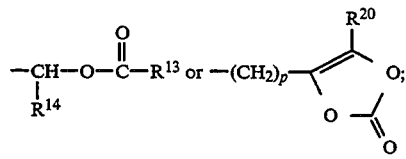

R¹³ and R¹⁴ are alkyl;
R²⁰ is alkyl; and
p is 1.

DETAILED DESCRIPTION OF THE INVENTION

The present invention relates to the compounds of formula I and to pharmaceutical compositions and methods employing such compounds.

Listed below are definitions of terms used in this specification. These definitions apply to the terms as used throughout this specification, either individually or as part of a larger group, unless otherwise limited in specific instances.

The term "aryl" or "ar" refers to unsubstituted phenyl and phenyl substituted with 1, 2 or 3 groups selected from halogen, alkyl, alkoxy, alkylthio, hydroxy, alkanoyl, nitro, amino, dialkylamino and trifluoromethyl. Unsubstituted and monosubstituted phenyl are preferred and unsubstituted phenyl is the most preferred.

The term "alkyl" refers to straight or branched chain groups having 1 to 10 carbon atoms. Alkyl groups having 1 to 4 carbon atoms are preferred.

The term "cycloalkyl" refers to cyclic hydrocarbon groups having 3 to 8 carbon atoms.

The term "alkoxy" refers to straight or branched chain groups having 1 to 8 carbon atoms. Alkoxy groups having 1 to 3 carbon atoms are preferred.

The terms "halogen" and "halo" refer to fluorine, chlorine, bromine and iodine, with fluorine and chlorine preferred.

The terms "haloalkyl" and "haloalkoxy" refer to groups of 1 to 4 carbon atoms substituted with one or more halogen atoms. Exemplary haloalkyl groups are —CF₃, —CH₂CF₃ and C₂F₅.

It should be understood that the present invention is meant to include prodrug forms, such as ester, acetal and/or mixed acetal derivatives of compound I. For example, such derivatives have been documented in *Design of Prodrugs*, edited by H. Bundgard, (Elsevier, 1985) and *Methods in Enzymology*, Vol. 42, p. 309–396, edited by K. Widder et al. (Academic Press, 1985). While prodrug forms of compound I are generally represented herein (e.g., wherein R⁹ is alkyl), it is understood that any moiety at R⁷ that will be cleaved in vivo to provide an acidic R⁷ moiety is within the scope and spirit of the invention.

Compound I may be prepared by the following exemplary process.

A diamine

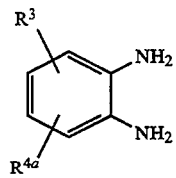

(wherein R⁴ᵃ is R⁴ other than R⁸—CO₂H) is coupled with a halide-ester

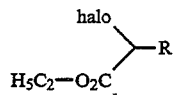

by treatment with a carbonate (e.g., potassium carbonate) in an organic solvent (e.g., dimethylformamide), followed by an oxidant (e.g., manganese dioxide) and a halogenating agent (e.g., phosphorus oxychloride) to form a substituted quinoxaline halide

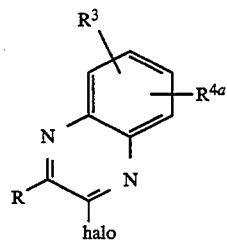

Quinoxaline halide III is treated with a strong oxidant and an acid (e.g., potassium persulfate sulfuric acid), followed by a biphenyl

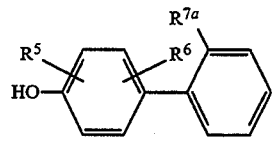

(wherein R⁷ᵃ is R⁷ other than —R⁸CO₂H) in the presence of a mild base (e.g., cesium carbonate) in an organic solvent (e.g., dimethylformamide) to form compound I wherein X is O, R² is O and R¹ is absent. For R⁷=—R⁸CO₂H, the so-formed compound is treated with a de-esterifying agent such as trifluoroacetic acid.

Compound I wherein R⁹ is alkali metal or ammonium can be prepared by treating the corresponding acids with bases such as lithium carbonate or sodium carbonate.

Compound I wherein R⁹ is —CH(R¹⁴)—O—C-(O)—R¹³ is prepared by treating the associated free acid with a halide

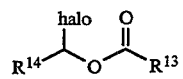

in the presence of a catalyst (e.g., silver carbonate or silver oxide followed by sodium bicarbonate) in an organic solvent (e.g., tetrahydrofuran, methanol). Likewise, compound I wherein R⁹ is

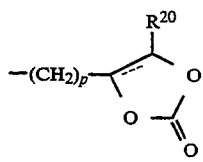

is prepared by treating the associated free acid compound I with a halide

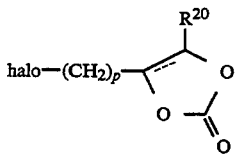

in the presence of a catalyst (e.g., silver oxide). Other $R^9$ substituents may be prepared by conventional esterification of the corresponding free acid.

Other $R^7$ substituents may be prepared by procedures described in European Patent Application 253,310 (Dupont), published Jan. 20, 1988.

Diamine II wherein $R^4$ is —$R^8$—$CO_2R^9$ may be prepared as follows. A nitro anhydride

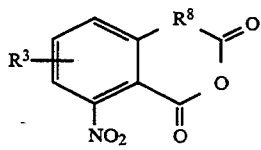

is treated with an ammonium (e.g., ammonium hydroxide) to form a nitro-amide-acid

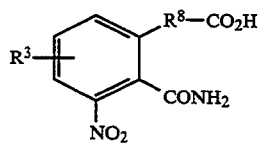

Nitro-amide-acid VIII is treated with halogen (e.g., $Br_2$) and an aqueous alkali metal hydroxide (e.g., sodium hydroxide) to form a nitro-amine-acid

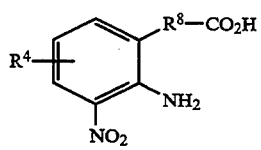

Nitro-amine-acid IX is treated with an esterifying agent (e.g., methyl iodide) in the presence of a catalyst (e.g., cesium carbonate) in an organic solvent (e.g., dimethylformamide) to form a nitro-amine-ester

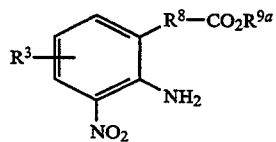

wherein $R^{9a}$ is $R^9$ other than hydrogen. Nitro-amine-ester X is hydrogenated in the presence of a catalyst (e.g., palladium on carbon) in an organic solvent or solvent mixture (e.g., methanolethyl acetate) to form diamine II wherein $R^4$ is —$R^8CO_2R^9$.

Alternatively, diamine II wherein $R^4$ is —$R^8$—$CO_2R^9$ may be prepared as follows. A phenyl halide

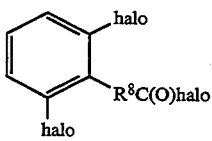

is treated with an alcohol

to form an ester

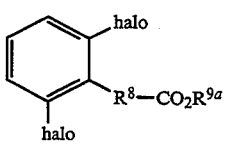

Ester XIII is treated with a nitro-forming agent (e.g., nitric acid) and an organic acid (e.g., sulfuric acid) to form a nitro-ester

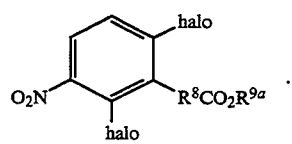

Nitro-ester XIV is treated with an aminating agent (e.g., aqueous ammonium hydroxide) to form nitro-amine-ester X, which may be hydrogenated as described previously herein to form diamine II.

Biphenyl IV may be prepared as follows. A phenylhalide

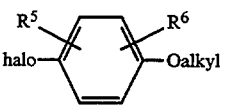

is treated with an alkylating agent (e.g., n-butyl lithium), followed by a dehydrating agent (e.g., zinc chloride), and a second phenylhalide

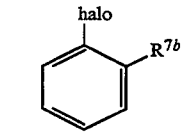

(wherein $R^{7b}$ is cyano or $R^7$ other than 5-tetrazolyl or —$R^8$—$CO_2H$) in the presence of a catalyst (e.g., palladium oxide). To form biphenyl IV wherein $R^7$ is 5-tetrazolyl, biphenyl IV wherein $R^{7b}$ is cyano may be treated in situ with a halide (e.g., boron tribromide)

and a trialkyltin azide (e.g., tributyltin azide) in an inert solvent (e.g., xylene) at about 90° to 110° C.

Compound I wherein X is —CH₂— may be prepared as follows. A bromobiphenyl

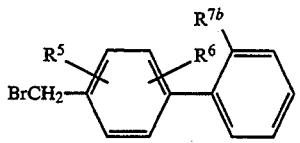
XVII is treated with a debrominating agent (e.g., silver borotetrafluoride) in an organic solvent (e.g., dimethyl sulfoxide), followed by an alkynylating agent (e.g., 1-hexyne), an alkylating agent (e.g., n-butyl lithium), and an acylating agent (e.g., acetic anhydride) to form a biphenyl acetate

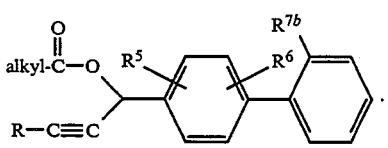
XVIII

Biphenyl acetate XVIII is further acylated by treatment with, for example, Pd(CH₃CN)₂Cl₂ in a biphasic solvent (e.g., tetrahydrofuran and water) to form a diacyl biphenyl

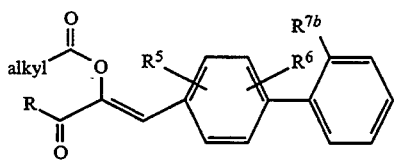
XIX

Diacyl biphenyl XIX is treated with a reducing agent (e.g., tetrabutylammonium hydroxide)in an organic solvent (e.g., acetonitrile) to form a biphenyl enol

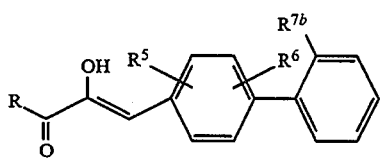
XX

Biphenyl enol XX is reacted with diamine II in an organic solvent, followed by a trialkyltin azide (e.g., tributyltin azide) in an inert solvent (e.g., xylene) at about 90° to 110° to form compound I wherein X is —CH₂— and R¹ and R² are absent. Compounds wherein X is —CH₂— and R⁷ is other than R⁷ᵇ may be prepared as described for compound I wherein X is O.

To form compounds wherein one or both R¹ and R² are O, the associated compound I wherein R¹ and R² are absent is treated with an oxidizing agent (e.g., metachloroperoxybenzoic acid) in an organic solvent (e.g., chloroform, methylene chloride).

The compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., such as humans. The compounds of this invention inhibit the action of AII at its receptors on target cells and thus prevent the increase in blood pressure produced by this hormone-receptor interaction. Thus by the administration of a composition containing one (or a combination) of the compounds of this invention, angiotensin-dependent hypertension in a species of mammal (e.g., humans) suffering therefrom is alleviated. A single dose, or preferably two to four divided daily doses, provides on a basis of about 0.1 to 100 mg per kilogram of body weight per day, preferably about 1 to 15 mg per kilogram of body weight per day, is appropriate to reduce blood pressure. The substance is preferably administered orally, but intranasal, transdermal and parenteral routes such as the subcutaneous, intramuscular, intravenous or intraperitoneal routes can also be employed.

The compounds of this invention are also useful in the treatment/prevention of congestive heart failure, cardiac hypertrophy, loss of congnitive function, renal failure and in conjunction with kidney transplant. In addition, in view of the role of these compounds in the renin-angiotensin system described above, the A-II antagonist compounds disclosed herein are also expected to be useful for the same or similar indications which have developed for ACE inhibitors.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, -stabilizer, flavor, etc., in a unit dosage form as called for by accepted pharmaceutical practice. The amount of active substance in these compositions or preparations is such that a suitable dosage in the range indicated is obtained.

The compounds of this invention can also be formulated in combination with a diuretic for the treatment of hypertension. A combination product comprising a compound of this invention and a diuretic can be administered in an effective amount which comprises a total daily dosage of about 30 to 600 mg (preferably about 30 to 330 mg) of a compound of this invention and about 15 to 300 mg (preferably about 15 to 200 mg) of the diuretic to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticryanfen, chlorthialidone, furosemide, musolimine, bumetanide, triamterene, amiloride and spironolactone and salts of such compounds.

The present invention may now be further described by the following examples, which are illustrative rather than limiting.

Example 1

2-Butyl-3-[[2'-(1H-tetrazol-5-yl)[1,1'-biphenyl]-4yl]oxy]quinoxaline

A. 2-Butyl-1,2-dihydro-3-oxoquinoxaline

A mixture of 1,2-phenylenediamine (10.8 g, 100 mmol), ethyl-2-bromohexanoate (22.3 g, 100 mmol) and potassium carbonate (13.8 g, 100 mmol) in dimethylformamide (50 mL) was stirred at room temperature overnight, and then at 120° C. for 3 hours. The reaction mixture was cooled to room temperature and filtered. The filtrate was concentrated in vacuo. The residue was purified by a flash chromatography column on silica gel eluting with hexane:ethyl acetate (3:1) to afford compound A as an oil, which solidified on standing at room temperature to give compound A (16.5 g, 81%).

Melting point: 90° to 91 ° C.

B. 2-Butyl-3-oxoquinoxaline

To a stirring solution of compound A (14.5 g, 71.0 mmol) in tetrahydrofuran (150 mL) at 0° C. was added manganese dioxide (25 g, 270 mmol) in several portions. The resulting mixture was stirred at room temperature overnight. Dimethylformamide (100 mL) was added to the reaction mixture, which was then was filtered through a Celite ® pad. Concentration in vacuo gave a solid, which was triturated with ether to obtain compound B (11.75 g, 82%).

Melting point: 153° to 154° C.

C. 2-Butyl-3-chloroquinoxaline

A mixture of compound B (10.0 g, 49.5 mmol) and phosphorous oxychloride (50 mL) was heated at 125° C. for 2 hours, and then was cooled to room temperature. The reaction mixture was slowly poured into a mixture of ice and sodium bicarbonate (about 140 g). The mixture was then partitioned between methylene chloride (100 mL) and water. The organic layer was taken and the aqueous layer was washed with methylene chloride (100 mL). The combined organic solution was dried over sodium sulfate and concentrated. The residue was purified by a flash chromatography column on silica gel eluting with 1% of ethyl acetate in hexane to afford compound C as an oil (9.5 g, 87%).

D. 4-(2-Cyanophenyl)anisole

To a solution of 4-bromoanisole (18.7 g, 0.1 mol) in anhydrous tetrahydrofuran (200 mL) at −78° C. was added a solution of n-butyl lithium (2.5M, 50 mL) in hexane. After stirring for 0.5 hours, a solution of the zinc chloride (1M, 100 mL) in ether was added. After the mixture was stirred for 1 hour at −78° C., tetrakis (triphenylphosphine) palladium (0.85 g, 0.73 mmol) and 2-bromobenzonitrile (18.2 g, 0.1 mol) were added. The reaction mixture was stirred at room temperature overnight, and then was concentrated in vacuo. The residue was partitioned between ethyl acetate (100 mL) and 1N hydrochloric acid (100 mL). The organic solution was washed with brine and dried over magnesium sulfate. Concentration in vacuo gave crude 4-(2-cyanophenyl)anisole, which was directly used for next reaction. The compound can be triturated with ether to obtain a pure solid product.

Melting point: 81° to 82° C.

E. 4-(2-Cyanophenyl)phenol

To a solution of compound D (the crude product) in methylene chloride (150 mL) at −78° C. was added boron tribromide (1M, 200 mL) in methylene chloride. After the addition, the resulting solution was stirred at room temperature overnight. The reaction was quenched by adding very slowly 100 mL of methanol at −78° C. The mixture was then poured into ice-water. Ethyl acetate (300 mL) was added to the aqueous mixture, and the organic layer was removed, washed with water and dried over magnesium sulfate. Concentration in vacuo gave a solid, which was triturated with ether to obtain compound E (11.5 g, 59% overall). If needed, the product can be also purified by silica gel column eluting with toluene/ethyl acetate (4:1).

Melting point: 177° to 178° C.

F. 2-Butyl-3-[[2′-cyano[1,1′-biphenyl]-4-yl]oxy]quinoxaline

A mixture of compound C (2.0 g, 9.1 mmol), compound E (1.77 g, 9.1 mmol) and cesium carbonate (5 g, 15.4 mmol) in dimethylformamide (10 mL) was stirred at 60° C. for 3 hours and the solid was filtered. The filtrate was concentrated in vacuo and the residue was triturated with ether to afford compound F as a solid (2.35 g, 68%).

Melting point: 136° to 137° C.

G. 2-Butyl-3-[[2′-(1H-tetrazol-5-yl)[1,1′-biphenyl]-4-yl]oxyquinoxaline

A mixture of compound F (1.50 g, 3.96 mmol) and tri-n-butyltin azide (2.63 g, 7.92 mmol) in xylene (10 mL) was stirred at 130° C for 48 hours. The reaction mixture was cooled to room temperature, loaded directly onto a flash chromatography column on silica gel, and eluted with hexane-ethyl acetate (5:1) followed by hexane:ethyl acetate:acetic acid (2:1:0.01) to afford Example 1 as a solid (1.22 g, 73%).

Melting point: 144° to 145° C. Rf=0.35 on silica gel plate in hexane:ethyl acetate:acetic acid (1:1:0.01).

Analysis Calculated for $C_{25}H_{22}N_6O \cdot 0.59H_2O$: Calc'd: C,69.33; H,5.39; N,19.40; Found: C,69.20; H,5.47; N,19.54

EXAMPLE 2

2-Butyl-3-[[2′-(1H-tetrazol-5-yl)[1,1′-biphenyl]-4-yl]oxy]quinoxaline, 4-oxide

A. 2-Butyl-3-chloroquinoxaline, 4-oxide

To a solution of compound C from Example 1 (1.10 g, 5.0 mmol) in concentrated sulfuric acid (5 mL) at 0° C. was added potassium persulfate (1.58 g, 5.85 mmol) with stirring. The resulting mixture was stirred at room temperature for 24 hours, poured into a mixture of ice and sodium acetate (2 g), and extracted with ethyl acetate (3×20 mL). The organic solution was dried over sodium sulfate and concentrated in vacuo. The residue was purified through a flash chromatography column on silica gel, eluted with hexane:ethyl acetate (10:1) to afford compound A as an oil (605 mg, 51%).

B. 4-[2-(1H-tetrazol-5-yl)phenyl]phenol

A mixture of compound E from Example 1 (1.15 g, 5.9 mmol) and tri-n-butyltin azide (7.0 g, 21.0 mmol) in xylene (20 mL) was stirred at 120° C. for 60 hours and then at 130° C. for 4 hours. The reaction mixture was cooled and directly loaded onto a flash chromatography column on silica gel eluting with about 1 L of hexane:acetic acid (100:1), followed by ethyl acetate to afford compound B as a solid (0.68 g, 48%).

Melting point: 230° C. (dec.).

C. 2-Butyl-3-[[2′-(1H-tetrazol-5-yl)[1,1′-biphenyl]-4-yl]oxy]quinoxaline, 4 oxide A mixture of compound A (185 mg, 0.78 mmol), compound B (186 mg, 0.78 mmol) and cesium carbonate (500 mg, 1.53 mmol) in dimethylformamide (1.5 mL) was stirred at room temperature for 24 hours under argon atmosphere. The reaction mixture was then poured into water and the aqueous solution was adjusted to pH 4 with acetic acid. The product was extracted with ethyl acetate (3×20 mL). The organic solution was dried over sodium sulfate and concentrated in vacuo and the residue was purified by preparative HPLC (column: YMC S-10 ODS 3×500 mm; flow rate 35 mL/min; mobile phase 76% methanol containing 0.1% of trifluoroacetic acid: UV 254 nm). The desired fractions were concentrated in vacuo to afford a solid (212 mg, 62%).

Melting point: 100° to 104° C. $R_f$=0.72 on silica gel TLC in 1% acetic acid in ethyl acetate by UV.

Calc'd for $C_{25}H_{22}N_6O_2 \cdot 0.13\ H_2O$: Calc'd: C,68.12; H,5.09; N,19.06 Found: C,68.25; H,5.09; N,18.93

EXAMPLE 3

2-Butyl-3-[[2'-(1H-tetrazol-5-yl)[1,1'-biphenyl]-4-yl]oxy]-quinoxaline-5-carboxylic acid; and

EXAMPLE 4

2-Butyl-3-[[2'-(1H-tetrazol-5-yl)[1,1'-biphenyl]-4-yl]oxy]-quinoxaline-5-carboxylic acid, methyl ester A. 2-Amino-3-nitrobenzoic acid, methyl ester 2-Amino-3-nitrobenzoic acid may be prepared as described in Chapman, E. and Stephen, H., "Preparation of phthalmic acids and their conversion to anthranilic acids," J. Chem. Soc., (1925), 1151. To a mixture of this acid (14.00 g, 76.9 mmol) and cesium carbonate (20.00 g, 61.5 mmol) in dimethylformamide (150 mL) at 0° C. methyl iodide (12.00 g, 84.5 mmol) was added with stirring. After 20 minutes, it was warmed to room temperature and stirred for 3 hours. Most of the solvent was removed in vacuo and the residue was partitioned between ethyl acetate (250 mL) and water (100 mL). The organic layer was separated, the aqueous layer was washed with ethyl acetate (250 mL) and the combined organic extract was dried over magnesium sulfate. After concentrating, the residue was triturated with ether to obtain the first crop of product as a yellow solid (3.20 g). The filtrate solution was concentrated, and the residue was passed through a flash column on silica gel eluting with 4:1 hexane:ethyl acetate to afford a slightly impure product. This material was triturated with methanol to obtain a pure second crop of product (9.10 g); total 12.3 g in 82% yield.

Melting point: 92°–93° C. Analysis for $C_8H_8N_2O_4$: Calc'd: C,48.98; H,4.11; N,14.28. Found: C,49.06; H,3.94; N,14.27.

B. 2,3-Diaminobenzoic acid, methyl ester

Reduction of nitro compound A (7.50 g, 38.2 mmol) in methanol (70 mL) and ethyl acetate (70 mL) in the presence of 10% palladium on carbon (1.50 g) under 50 psi of hydrogen gas was complete in 3 hours. The catalyst was filtered through a Celite® pad and washed with methanol to obtain the crude product (6.15 g, 95% yield). This diamino compound easily decomposes and so was used directly for the next step.

$^1$H NMR (CDCl$_3$) δ3.91 (s, 3H), 6.58 (t, J=8.2 Hz, 1H), 6.94 (d, J=8.2 Hz, 1H), 7.41 (d, J=8.2 Hz, 1H).

$^{13}$C NMR (CDCl$_3$) δ51.6, 101.9, 116.7, 120.7, 122.6, 128.5, 134.2, 170.8.

C. 2-Butyl-3-oxo-1,2,4-trihydroquinoxaline-5-carboxylic acid, methyl ester

A mixture of diamino compound B (6.15 g, 37.0 mmol), ethyl 2-bromohexanoate (7.80 g, 35.0 mmol) and sodium bicarbonate (1.00 g) in dimethylformamide (65 mL) was stirred at room temperature overnight, and then heated for 5 hours at 60° C. and 8 hours at 75° C. Thin layer chromatography showed several spots, and so 1.5 g of sodium hydride (60% dispersion) was added to the mixture. The reaction mixture was stirred for 3 hours at room temperature. It was mostly concentrated in vacuo and the residue was partitioned between chloroform (150 mL) and 1N hydrochloric acid (60 mL), the organic layer was taken and the aqueous layer was washed with chloroform (150 mL). The combined organic extract was dried over magnesium sulfate, concentrated and the residue was passed through a flash chromatography column on silica gel eluting with 3:1/hexane:ethyl acetate to obtain the desired product (3.1 g, 31% overall yield from compound A) as a light yellow solid.

Melting point: 78°–81° C.

D. 2-Butyl-4-hydro-3-oxoquinoxaline-5-carboxylic acid, methyl ester

A mixture of compound C (3.00 g, 11.5 mmol) and manganese dioxide (5.00 g) in tetrahydrofuran (30 mL) was heated at reflux temperature for 10 hours. The mixture was directly passed through a flash column on silica gel eluting with 4:1/hexane:ethyl acetate to obtain the product as a light orange colored solid (2.55 g, 85% yield).

Melting point: 67°–79° C.

E. 2-Butyl-3-chloroquinoxaline-5-carboxylic acid, methyl ester

A solution of compound D (2.30 g, 8.8 mmol) in phosphorous oxychloride (25 mL) was heated at reflux temperature for 2 hours. Most of excess phosphorous oxychloride was removed under reduced pressure, and the blue colored residue was made alkaline by use of aqueous sodium bicarbonate solution, which made the mixture red colored. The crude product was extacted using ethyl acetate (150 mL), and the aqueous layer was washed with chloroform (100 mL). The combined organic solution was dried over magnesium sulfate, concentrated and the residue was passed through a flash chromatography column on silica gel eluting with 4:1 hexane:ethyl acetate to obtain the product as a red-colored oil (1.48 g, 60% yield). The red color comes from the very minute amount of impurity which was inseparable from the desired product. However, the NMR spectrum of this material did not exhibit any impurity peaks.

$^1$H NMR (CDCl$_3$) δ1.08 (t, J=7.6 Hz, 3H), 1.58 (sx, J=7.6 Hz, 2H), 1.94 (qn, J=7.6 Hz, 2H), 3.22 (d, J=7.8 Hz, 1H), 3.26 (d, J=7.6 Hz, 2H), 4.13 (s, 3H), 7.84 (dd, J$_1$=7.8 Hz, J$_2$=7.6 Hz, 1H), 8.21 (d, J=7.7 Hz, 1H), 8.27 (d, J=7.7 Hz, 1H).

$^{13}$C NMR (CDCl$_3$) δ13.9, 22.6, 29.4, 35.6, 52.7, 128.9, 130.3, 131.4, 132.4, 138.0, 140.8, 148.2, 156.8, 165.9.

F. 2-Butyl-3-[[2'-(1H-tetrazol-5-yl)[1,1'-biphenyl]-4-yl]oxy]quinoxaline-5-carboxylic acid; and 2-Butyl-3-[[2'-(1H-tetrazol-5-yl)[1,1'-biphenyl]-4-yl]oxy]-quinoxaline-5-carboxylic acid, methyl ester A mixture of biphenyl B from Example 2 (1.05 g, 4.4 mmol), quinoxaline E (1.23 g, 4.4 mmol) and cesium carbonate (3.25 g, 9.9 mmol) in dimethylformamide (9 mL) was heated at 90 C. for 1 day. Most of the solvent was removed under reduced pressure and the residue was acidified using 4N hydrochloric acid. The crude product was extacted with chloroform (200 mL), dried over sodium sulfate, and concentrated, and the residue was purified by preparative HPLC to obtain Example 4 (965 mg, 46% yield) and Example 3 (210 mg, 10% yield) as a white solid.

Melting point of Example 3: 240°–241° C. Preparative HPLC condition: (YMC S-10 ODS 30×500 mm, 78% methanol in water containing 0.1% trifluoroacetic acid, 56 mL/minute flow rate, 254 nm. Rt of Example 3=25 minutes. Rt of Example 4=35 minutes).

EXAMPLE 3

$^1$H NMR (d$_6$-DMSO) δ0.99 (t, J=7.0 Hz, 3H), 1.50 (sx, J=7.0 Hz, 2H), 1.89 (qn, J=7.0 Hz, 2H), 3.12 (d, J=7.6 Hz, 1H), 3.15 (d, J=6.6 Hz, 1H), 7.26 (d, J=8.2 Hz, 2H), 7.45 (d, J=8.2 Hz, 2H), 7.60–7.85 (m, 5H), 8.26 (d, J=7.6 Hz, 2H).

$^{13}$C NMR (d$_6$-DMSO) δ13.9, 22.0, 28.5, 32.4, 121.3, 125.3, 127.3, 128.0, 130.4, 130.6, 130.7, 131.2, 132.1,132.6, 135.7, 137.1, 138.4, 140.6, 151.4, 152.3, 154.7, 165.9; MS (M+H)+467, (M−H)−465; Analysis for C$_{26}$H$_{22}$N$_6$O$_3$: Calc'd: C,66.94; H,4.75; N,18.02. Found: C,67.05; H,4.77; N,18.15.

EXAMPLE 4

$^1$H NMR (d$_6$-DMSO) δ0.99 (t, J=7.0 Hz, 3H), 1.47 (sx, J=7.0 Hz, 2H), 1.86 (qn, J=7.0 Hz, 2H), 3.10 (d, J=7.6 Hz, 1 H), 3.15 (d, J=6.6 Hz, 1H), 3.67 (s, 3H), 7.24 (d, J=8.2 Hz, 2H), 7.43 (d, J=8.2 Hz, 2H), 7.55–7.85 (m, 5H), 7.96 (dd, J$_1$=7.0 Hz, J$_2$=1.2 Hz, 1H), 8.15 (dd, J$_1$=7.0 Hz, J$_2$=1.2 Hz, 1H).

$^{13}$C NMR (CDCl$_3$) δ14.4, 23.1, 30.1, 33.7, 53.1, 122.8, 123.1, 126.9, 127.8, 128.7, 130.6, 131.1, 131.5, 131.9, 132.4, 133.0, 136.6, 138.0, 139.7, 140.8, 152.2, 153.3, 156.4, 167.0.

Example 5

2-Butyl-3-[[2'-(1H-tetrazol-5-yl)[1,1'-biphenyl]-4-yl]oxy]quinoxaline-5-carboxylic acid, ethyl ester A. 2-Amino-3-nitrobenzoic acid, ethyl ester A mixture of 2-amino-3-nitrobenzoic acid (16.5 g, 0.091 mol), ethyl iodide (21.2 g, 0.136 mol) and cesium carbonate (29.5 g, 0.091 mol) in dimethylformamide (250 mL) was stirred at room temperature for 16 hours. The reaction mixture was then diluted with methylene chloride (250 mL) and filtered. The filtrate was concentrated under reduced pressure, and the residue was partitioned between 5% of aqueous sodium bicarbonate (100 mL) and methylene chloride (300 mL). The organic phase was washed with brine and dried over sodium sulfate. Concentration and trituration of the residue with ethyl ether gave ester A as a solid.

Melting point: 104°–105° C., 17.4 g (91%).

B. 2,3-Diaminobenzoic acid, ethyl ester

Compound A (16.0 g, 0.076 mol) in ethyl acetate (70 mL) and ethanol (70 mL) was hydrogenated over 10% palladium on carbon as a catalyst under hydrogen (40 psi) at room temperature for 3 hours. It was filtered and concentrated under reduced pressure to afford an oil, which was solidified upon standing at room temperature (it turned dark in the air.).

Melting point: 50°–51° C., 13.6 g (99%).

C. 2-Butyl-3-oxo-1,2,4-trihydroquinoxaline-5-carboxylic acid, ethyl ester

A mixture of diamine B (13.4 g, 0.074 mol), ethyl 2-bromohexanoate (24.8 g, 0.11 mol) and sodium bicarbonate (6.8 g, 0.081 mol) was stirred in dimethylformamide (50 mL) at 120° C. for 48 hours. It was then cooled to room temperature and diluted with ethyl acetate (200 mL). The organic mixture was washed with water (3×100 mL), dried over sodium sulfate and concentrated. The residue was purified by a flash chromatography column on silica gel eluting with hexane/ethyl acetate (4:1) to afford compound C as a solid, 17.5 g (85%).

D. 2-Butyl-4-hydro-3-oxoquinoxaline-5-carboxylic acid, ethyl ester

To a solution of compound C (17.5 g, 0.063 mol) in tetrahydrofuran (150 mL) was added manganese dioxide (20 g, 0.23 mol). The mixture was stirred at reflux temperature for 40 hours. The solid was filtered through a Celite® pad and the filtrate was concentrated. The residue was purified by a column chromatography on silica gel eluting with hexane/ethyl acetate (4:1) to afford compound D as a solid.

Melting point 78°–79° C., 13.4 g (77%).

E. 2-Butyl-3-chloroquinoxaline-5-carboxylic acid, ethyl ester

Quinoxalinone D (3.0 g, 0.011 mol) was dissolved in phosphorus oxychloride (20 mL) and the mixture was refluxed for 1 hour. The excess phosphorus oxychloride was removed under reduced pressure. The residue was neutralized with 5% aqueous sodium bicarbonate solution and extracted with ethyl acetate (50 mL). The extract was dried over sodium sulfate and concentrated. The residue was chromatographed on silica gel eluting with hexane/ethyl acetate (10:1) to afford compound E (2.65 g) as an oil with a trace amount of red colored impurity (83% yield).

$^1$H NMR (CDCl$_3$) δ8.22 (d, J=8.2 Hz, 1H), 8.16 (d, J=7.6 Hz, 1H), 7.75 (dd, J=8.2 Hz, J=7.6 Hz, 1H), 4.55 (q, J=7.6 Hz, 2H), 3.13 (t, J=7.6 Hz, 2H), 1.85 (qn, J=7.6 Hz, 2H), 1.46 (m, 5H), 1.00 (t, J=7.6 Hz, 3H).

$^{13}$C NMR (CDCl$_3$) δ165.9, 156.6, 148.5, 140.6, 138.3, 132.1, 130.9, 130.2, 128.8, 61.5, 35.4, 29.5, 22.4, 14.2, 13.7.

F. 2-Butyl-3-[[2'-(1H-tetrazol-5-yl)[1,1'-biphenyl]-4-yl]oxy]-quinoxaline-5-carboxylic acid, ethyl ester A mixture of compound E (500 mg, 1.71 mmol), biphenyl B from Example 2 (407.0 mg, 1.71 mmol) and cesium carbonate (557 mg, 1.71 mmol) in dimethylformamide (2 mL) was stirred at 85° C. for 20 hours. The mixture was cooled to room temperature and acidified with 2N of aqueous hydrochloric acid solution to pH 2. It was extracted with ethyl acetate (50 mL). The extract was washed with brine, dried over sodium sulfate and concentrated. The residue was chromatographed on silica gel eluting with hexane/ethyl acetate (1:1) to afford Example 5 as an oil, 740.0 mg (88%).

$^1$H NMR (CDCl$_3$) δ8.09 (m, 2H), 7.90 (dd, J=1.1 Hz, J=7.6 Hz, 1H), 7.63–7.34 (m, 3H), 7.18 (d, J=8.2 Hz, 2H), 7.00 (d, J=8.2 Hz, 2H), 4.26 (q, J=7.6 Hz, 2H), 3.09 (t, J=7.6 Hz, 2H), 1.87 (qn, J=7.7 Hz, 2H), 1.51 (sx, J=7.6 Hz, 2H), 1.18 (t, J=7.6 Hz, 3H), 1.01 (t, J=7.6 Hz, 3H).

$^{13}$C NMR (CDCl$_3$) δ166.9, 155.9, 152.9, 152.1, 140.8, 139.7, 137.5, 136.2, 132.6, 131.6, 1 31.3, 130.9, 130.3, 128.6, 128.3, 126.7, 123.1, 122.2, 62.0, 33.6, 29.9, 23.0, 14.4, 14.3.

EXAMPLE 6

2-Butyl-3-[[2'-(1H-tetrazol-5-yl)[1,1'-biphenyl]-4-yl]oxy]-quinoxaline-5-carboxylic acid, ethyl ester, 1-oxide A solution of Example 5 (590 mg, 1.19 mmol) and solution of m-chloroperoxybenzoic acid (300 mg, 80–85% content) in methylene chloride (5 mL) was stirred at room temperature for 16 hours. The mixture was filtered and the filtrate was concentrated. The residue was purified by preparative HPLC (column: YMC S-10 ODS 30×500 mm; flow rate: 37 ml/min; solvent system: 74% aqueous methanol containing 0.1% trifluoroacetic acid; UV 254 nm) to afford Example 6 as a solid, 450 mg (88%).

Melting point: 93°–96° C. $R_f$=0.79, silica gel plate, 1% acetic acid in ethyl acetate by UV. HPLC: $R_t$=8.32 minutes at 254 nm, solvent system 78.0% aqueous methanol containing 0.2% phosphoric acid, 1.5 mL/minutes flow rate in YMC S3-ODS column (6.0×150 mm).

$^1$H NMR (CDCl$_3$) δ8.70 (dd, J=1.7 Hz, J=8.2 Hz, 1H), 8.18 (d, J=7.0 Hz, 1H), 8.03 (d, J=7.6 Hz, 1H), 7.70–7.45 (m, 4H), 7.25 (d, J=8.8 Hz, 2H), 7.18 (d, J=8.8 Hz, 2H), 4.30 (q, J=7.6 Hz, 2H), 3.30 (t, J=7.6 Hz, 2H), 1.83 (qn, J=7.6 Hz, 2H), 1.58 (sx, J=7.6 Hz, 2H), 1.24 (t, J=7.6 Hz, 3H), 1.06 (t, J=7.6 Hz, 3H).

$^{13}$C NMR (CDCl$_3$) δ165.7, 158.3, 152.4, 140.3, 137.9, 137.4, 136.3, 135.1, 132.9, 131.2, 130.9, 130.5, 130.2, 130.0, 129.3, 128.1, 126.6, 122.8, 122.2, 61.9, 27.2, 24.7, 22.9, 14.0, 13.8; MS 511 (M+1H)$^+$, 495 (M+H−O)$^+$.

Analysis for C$_{28}$H$_{26}$N$_6$O$_4$. 0.24H$_2$O: Calc'd: C, 65.32; H, 5.18; N, 16.32. Found: C, 65.62; H, 5.18; N, 16.02.

EXAMPLE 7

2-Butyl-3-[[2'-(1H-tetrazol-5-yl)[1,1'-biphenyl]-4-yl]oxy]-quinoxaline-5-carboxylic acid, methyl ester, 1-oxide A mixture of Example 4 (560 mg, 1.17 mmol) and m-chloroperoxybenzoic acid (323 mg of 80–85% purity) in dichloromethane (5 mL) was stirred overnight at room temperature. The reaction mixture was directly loaded onto preparative HPLC to obtain the desired N-oxide Example 7 (356 mg, 62% yield) as a white solid. Prep. HPLC condition: YMC S-10 ODS 30×500 mm, 78% methanol in water containing 0.1% trifluoroacetic acid, 35 mL/min. flow rate, 254 nm, Rt=25 minutes.

$^1$H NMR (CD$_3$OD) δ1.06 (t, J=7.0 Hz, 3H), 1.57 (sx, J=7.0 Hz, 2H), 1.84 (qn, J=7.0 Hz, 2H), 3.28 (d, J=7.6 Hz, 1H), 3.35 (d, J=6.7 Hz, 1H), 3.80 (s, 3H), 7.29 (d, J=8.8 Hz, 2H), 7.42 (d, J=8.8 Hz, 2H), 7.60–7.80 (m, 5H), 8.04 (d, J=8.8 Hz, 1H), 8.62 (d, J=8.8 Hz, 1H). $^{13}$C NMR (CD$_3$OD) δ14.2, 24.0, 25.6, 28.2, 53.2, 122.8, 128.1, 129.5, 131.1, 131.7, 132.0, 132.6, 133.1, 136.1142.7.

Example 8

2-Butyl-3-[[2'-(1H-tetrazol-5-yl)[1,1'-biphenyl]-4-yl]oxy]quinoxaline-5-carboxylic acid, 1-oxide A mixture of N-oxide ester Example 7 (300 mg, 0.60 mmol), 2 mL of 1N sodium hydroxide and water (2 mL) in methanol (5 mL) was stirred overnight at room temperature. The reaction mixture was acidified using 4N hydrochloric acid to pH about 3, which caused the precipitation of the product. The solid was filtered, washed with water and methanol to obtain the first crop of Example 8 (195 mg) as a white solid. From the mother liquor, an additional 45 mg of the product was obtained, total 240 mg in 83% yield.

Melting point: 218°–220° C. (decomp.).

$^1$H NMR (d$_6$-DMSO) δ0.96 (t, J=7.0 Hz, 3H), 1.48 (sx, J=7.0 Hz, 2H), 1.73 (qn, J=7.0 Hz, 2H), 3.17 (t, J=7.0 Hz, 2H), 3.34 (broad, 1H), 7.25 (d, J=8.8 Hz, 2H), 7.42 (d, J=8.8 Hz, 2H), 7.60–7.82 (m, 5H), 8.30 (dd, J1=7.0 Hz, J2=1.8 Hz, 1H), 8.60 (dd, J$_1$=8.2 Hz, J$_2$=1.8 Hz, 1H).

$^{13}$C NMR (d$_6$-DMSO) δ13.7, 22.3, 24.2, 26.6, 121.2, 122.7, 123.5, 126.7, 127.4, 128.0, 130.4, 130.7, 130.8, 131.2, 133.5, 134.8, 136.8, 137.1, 137.4, 140.5, 151.4, 157.8, 165.6; MS (M+H)$^+$483, (M+H−O)+467;

Analysis for C$_{26}$H$_{22}$N$_6$O$_4$.0.19H$_2$O: Calc'd: C,64.27; H,4.64; N,17.29. Found: C,64.30; H,4.62; N,17.26.

EXAMPLE 9

2-Butyl-3-[4-[2-(1H-tetrazol-5-yl)phenyl]phenylmethyl]quinoxaline, sodium salt

A. 4-(2-Cyanophenyl)benzaldehyde

A mixture of crude 2-[4-(bromomethyl)phenyl]-phenylnitrile (32 g, 0.12 mol) sodium bicarbonate (20 g, 0.24 mol) and silver borotetrafluoride (25 g, 0.13 mol) in dimethyl sulfoxide (300 mL) was stirred at room temperature overnight. The solid was filtered and the solid was washed with methylene chloride. The combined filtrate was concentrated and the residue was partitioned between water (200 mL) and methylene chloride (300 mL). The organic layer was dried over sodium sulfate and concentrated in vacuo. The residue was triturated with diisopropyl ether to afford Compound A as a solid.

Melting point: 156°–157° C., 11.50 g (47%).

B. 1-[4-(2-Cyanophenyl)phenyl]-2-heptyn-1-yl acetate

To a solution of hexyne (1.97 g, 24 mmol) in tetrahydrofuran (20 mL) at 0° C. was added a solution of butyl lithium (9.6 mL of 2.5M in hexane, 24 mmol). This lithium salt solution was added to a suspension of compound A (4.14 g, 20 mmol) in tetrahydrofuran (30 mL) at 0° C. with stirring. After 1 hour, acetic anhydride (2.45 g, 2 4 mmol) was added at 0° C. and stirred for 0.5 hours. The mixture was partitioned between ethyl acetate (100 mL) and water (100 mL). The organic layer was washed with brine (50 mL) and dried over sodium sulfate. The residue, after concentration in vacuo, was purified through flash column chromatography on silica gel eluting with hexane-ethyl acetate (6:1) to afford acetate B as an oil, 6.3 g (95%).

$^1$H NMR (CDCl$_3$) δ7.73–7.37 (m, 8H), 6.53 (t, J=1.7 Hz, 1H), 2.26 (m, 2H), 2.07 (s, 3H), 1.54–1.36 (m, 4H), 0.89 (t, J=7.6 Hz, 3H).

$^{13}$C NMR (CDCl$_3$) δ169.1, 144.1, 137.9, 137.7, 133.2, 132.4, 129.6, 128.5, 127.6, 127.4, 118., 110.6, 88.1, 76.1, 65.0, 29.9, 21.4, 20.5, 18.0, 13.1.

C. 1-[4-(2-Cyanophenyl)phenyl]-3-oxo-1-hepten-2-yl acetate

A mixture of Compound B (5.6 g, 17 mmol) and Pd(CH$_3$CN)$_2$Cl$_2$ (4.40 g, 17 mmol) in tetrahydrofuran (40 mL) under argon was stirred at room temperature for 1 hour. To this solution was added water (1 mL) and the mixture was stirred for 2 hours at room temperature. It was then filtered through a celite pad. The filtrate was concentrated and the residue was purified through a flash chromatography column on silica gel eluting with hexane/ethyl acetate (4:1) to afford compound C as an oil, 3.62 g (61%).

$^1$H NMR (CDCl$_3$) δ7.78–7.44 (m, 8H), 7.22 (s, 1H), 2.78 (t, J=7.6 Hz, 2H), 2.36 (s, 3H), 1.68 (qn, J=7.6 Hz, 2H), 1.39 (sx, J=7.6 Hz, 2H), 0.94 (t, J=7.6 Hz, 3H).

$^{13}$C NMR (CDCl$_3$) δ194.4, 168.3, 145.1, 144.0, 139.2, 133.7, 132.8, 132.3, 130.3, 129.7, 129.0, 127.9, 125.9, 118.3, 110.8, 36.8, 26.1, 22.1, 20.5, 13.7.

D. 2-Butyl-3-[4-(2-cyanophenyl)phenylmethyl]quinoxaline

To a solution of compound C (1.53 g, 4.4 mmol) in acetonitrile (15 mL) at 0° C. was added dropwise an aqueous solution of 40% tetrabutylammonium hydroxide (3 mL). After the completion of the addition the mixture was stirred at 0° C. for 0.5 hours and was acidified with aqueous hydrochloric acid (4N) to pH 4. The solution was then partitioned between ethyl acetate (50 mL) and brine (50 mL). The organic phase was washed with brine (50 mL), dried over sodium sulfate, and concentrated in vacuo. The residue obtained here and 1,2-phenyldiamine (0.71 g, 8.8 mmol) were dissolved into toluene (15 mL), and stirred at reflux temperature for 1 hour. The reaction mixture was concentrated and chromatographed on silica gel eluting with hexane/ethyl acetate (4:1) to afford compound D as a solid.

Melting point: 98°–99° C., 0.81 g (49%).

E. 2-Butyl-3-[4-[2-(1H-tetrazol-5-yl)phenyl]phenylmethyl]quinoxaline

A mixture of compound D (850 mg, 2.25 mmol) and tri-n-butyltin azide (2.65 g, 7.98 mmol) in xylene (3 mL) was heated at 130° C. for 48 hours. The mixture was cooled to room temperature and purified through a flash chromatography column on silica gel eluting with hexane/acetic acid (100:1) followed by hexane/ethyl acetate/acetic acid (2:1:0.01) to afford compound E as a gum, 830 mg (88%).

$^1$H NMR (CDCl$_3$) δ14.6 (br.s, 1H), 7.93–7.83 (m, 2H), 7.70–7.11 (m, 6H), 6.93 (d, J=7.6 Hz, 2H), 6.83 (d, J=7.6 Hz, 2H), 4.18 (s, 2H), 2.78 (t, J=7.6 Hz, 2H), 1.56 (qn, J=7.6 Hz, 2H), 1.31 (sx, J=7.6 Hz, 2H), 0.84 (t, J=7.6 Hz, 3H).

$^{13}$C NMR (CDCl$_3$) δ157.2, 155.7, 154.4, 141.4, 141.0, 140.7, 137.7, 131.5, 130.9, 129.7, 129.4, 129.2, 128.5, 128.4, 128.1, 125.5, 122.9, 41.3, 35.0, 30.9, 22.9, 14.1.

F. 2-Butyl-3-[4-[2-(1H-tetrazol-5-yl)phenyl]phenylmethyl]quinoxaline, sodium salt Tetrazole E (80 mg, 0.19 mmol) was dissolved in methanol (1 mL) containing 0.2 mL of 1N aqueous sodium hydroxide solution. The basic solution was passed through a column chromatography on HP-20 eluting with water (100 mL), followed by 70% aqueous methanol to collect the desired fractions. Concentration in vacuo gave a solid.

Melting point: 135°–142° C., 63 mg (75%). R$_f$=0.67 in 1% acetic acid in ethyl acetate by UV, silica gel plate. HPLC R$_t$=8.0 minutes at 254 nm; solvent system 78% aqueous methanol containing 0.2% phosphoric acid, 1.5 mL/min. flow rate in YMC S3-ODS column (6×150 mm).

$^1$H NMR (CD$_3$OD) δ8.21–8.13 (m, 2H), 7.94–7.87 (m, 2H), 7.67–7.51 (m, 4H), 7.21 (s, 4H), 4.54 (s, 2H), 3.07 (t, J=7.6 Hz, 2H), 1.77 (qn, J=7.6 Hz, 2H), 1.53 (sx, J=7.6 Hz, 2H), 1.06 (t, J=7.6 Hz, 3H).

$^{13}$C NMR (CD$_3$OD) δ163.4, 159.4, 157.0, 143.6, 141.8, 138.1, 132.5, 131.8, 131.3, 130.6, 130.0, 129.7, 128.6, 43.0, 36.5, 32.3, 24.4, 14.9; MS (FAB) 465 (M+2Na−1H)+, 443 (M+Na)+, 421 (M+1H)+.

Analysis for C$_{26}$H$_{23}$N$_6$Na. 2.41 H$_2$O: Calc'd: C, 64.26; H, 5.77; N, 17.29; Found: C, 64.49; H, 5.47; N, 17.07.

EXAMPLE 10

2-Butyl-3-[4-[2-(1H-tetrazol-5-yl)phenyl]phenylmethyl]quinoxaline, 4-oxide;

EXAMPLE 11

2-Butyl-3-[4-[2-(1H-tetrazol-5-yl)phenyl]phenylmethyl]quinoxaline, 1-oxide; and

EXAMPLE 12

2-Butyl-3-[4-[2-(1H-tetrazol-5-yl)phenyl]phenylmethyl]quinoxaline, 1,4-dioxide

A mixture of compound E from Example 9 (520 mg, 1.24 mmol) and m-chloroperoxybenzoic acid (250 mg, 85% content) in methylene chloride (5 mL) was stirred at room temperature for 6 hours. The mixture was filtered and the solution was concentrated. The residue was purified by preparative HPLC (column: YMC S-10 ODS 30×500 mm; flow rate: 37mL/min; solvent system: 74% aqueous methanol containing 0.1% trifluoroacetic acid; UV 254 nm.) to obtain Examples 10, 11 and 12.

Example 10: melting point 160°–161° C., 250 mg (46%). R$_f$=0.71 in 1% acetic acid in ethyl acetate by UV; R$_t$=7.67 minutes at 254 nm, solvent system 75.6% aqueous methanol containing 0.2% phosphoric acid, flow rate 1.5 mL/min in YMC S3-ODS (6.0×50 mm).

$^1$H NMR (CDCl$_3$) δ8.29 (d, J=8.8 Hz, 1H), 8.01 (d, J=8.2 Hz, 1H), 7.87 (d, J=7.0 Hz, 1H), 7.76–7.34 (m, 5H), 7.07 (d, J=8.2 Hz, 2H), 6.96 (d, J=8.2 Hz, 2H), 4.45 (s, 2H), 3.00 (t, J=7.6 Hz, 2H), 1.76 (qn, J=7.6 Hz, 2H), 1.44 (sx, J=7.6 Hz, 2H), 0.94 (t, J=7.6 Hz, 3H).

$^{13}$C NMR (CDCl$_3$) δ158.8, 143.1, 141.2, 140.9, 137.9, 135.9, 135.1, 131.2, 130.8, 129.5, 129.1, 128.7, 128.0, 122.7, 118.8, 35.74, 32.2, 30.8, 22.64, 13.9; MS (negative) 436 (M)−, 420 (M−O)−.

Analysis for C$_{26}$H$_{24}$N$_6$O. 0.08H$_2$O: Calc'd: 71.23; H, 5.56; N, 19.19; Found: C, 71.23; H, 5.49; N, 19.27.

Example 11: melting point 175°–176° C. R$_f$=0.68 in 1% acetic acid in ethyl acetate on silica gel by UV, silica gel plate. R$_t$=6.71 minutes at 254 nm, solvent system 75.6% aqueous methanol containing 0.2% phosphoric acid, 1.5 mL/min flow rate in YMC S3-ODS (6.0×150 mm).

$^1$H NMR (CDCl$_3$) δ8.47 (d, J=8.2 Hz, 1H), 8.08 (d, d=8.2 Hz, 1H), 8.01 (d, J=7.0 Hz, 1H), 7.79–7.36 (m, 5H), 7.21 (d, J=7.6 Hz, 2H), 7.10 (d, J=7.6 Hz, 2H), 4.37 (s, 2H), 3.03 (t, J=5.9 Hz, 2H), 1.49 (m, 4H), 0.91 (t, J=5.9 Hz, 3H).

$^{13}$C NMR (CDCl$_3$) δ155.8, 154.9, 144.1, 140.8, 138.2, 137.3, 135.9, 131.3, 131.2, 130.7, 130.6, 130.0, 129.5, 129.4, 129.0, 128.3, 122.5, 118.8, 41.7, 27.3, 27.1, 23.1, 13.8; MS (positive) 437 (M+H)+, 421 (M−O)+.

Analysis for C$_{26}$H$_{24}$N$_6$O.0.05H$_2$O: Calc'd: C, 71.40; H, 5.55; N, 19.22; Found: C, 71.42; H, 5.51; N, 19.20.

Example 12: melting point 133°–134° C., 160 mg (93%). R$_f$=0.43, silica gel, 1% of acetic acid in ethyl acetate by UV, silica gel plate. R$_t$=6.51 minutes at 254 nm, solvent system 78.0% aqueous methanol containing 0.2% phosphoric acid, 1.5 mL/min flow rate in YMC S3-ODS column (6.0×150 mm).

$^1$H NMR (CDCl$_3$) δ8.58 (d, J=8.2 Hz, 1H), 8.45 (d, J=8.2 Hz, 1H), 7.95–7.36 (m, 6H), 7.18 (d, J=8.2 Hz, 2H), 7.06 (d, J=8.2 Hz, 2H), 4.49 (s, 2H), 3.15 (t, J=7.6 Hz, 2H), 1.64 (qn, 2H), 1.50 (sx, J=7.6 Hz, 2H), 0.96 (t, J=7.6 Hz, 3H)

$^{13}$C NMR (CDCl$_3$) δ168.7, 155.0, 146.1, 143.5, 140.7, 138.3, 137.3, 136.6, 135.3, 133.4, 131.9, 131.7, 131.3, 130.8, 130.1, 127.8, 129.6, 128.8, 128.1, 122.6, 120.2, 120.1, 33.2, 28.3, 27.7, 23.0, 13.7; MS 453 (M+H)+.

Analysis for C$_{26}$H$_{24}$N$_6$O$_2$.0.50H$_2$O: Calc'd: C, 67.68; H, 5.46; N, 18.21. Found: C, 67.93; H, 5.13; N, 17.96.

EXAMPLE 13

2-Butyl-6-ethoxy-3-[[2'-(1H-tetrazol-5-yl)[1,1'-biphenyl]-4-yl]oxy]quinoxaline-5-carboxylic acid, methyl ester A. 2,6-Difluorobenzoic acid, ethyl ester A neat liquid of 2,6-difluorobenzoyl chloride (25.0 g, 141.7 mmol) was added slowly to ethanol (250 mL) at ice bath temperature (0°–4° C.) with stirring. The mixture was stirred for 30 minutes at ice bath temperature and for 30 minutes at room temperature. It was concentrated in vacuo to obtain ester A (25.2 g, 96% yield) as an oil.

¹H NMR (CDCl₃) δ1.49 (t, J=7.0 Hz, 3H), 4.55 (q, J=7.0 Hz, 2H), 7.05 (t, J=8.2 Hz, 2H), 7.45-7.55 (m, 1H).

¹³C NMR (CDCl₃) δ13.9, 61.9, 111.7 (d, J=25.5 Hz), 132.3, 132.5 (d, J=10.0 Hz), 160.4 (d, J=256.3 Hz), 162.4.

B. 2,6-Difluoro-5-nitrobenzoic acid, ethyl ester

To cold concentrated nitric acid (1.2 g) at ice bath temperature concentrated sulfuric acid (1.6 mL) was added slowly. After stirring the mixture for 5 minutes, compound A (1.1 g, 5.9 mmol) was added, and the reaction mixture was warmed to room temperature. After 30 minutes, the mixture was poured into ice water (30 mL) and the product was extracted into dichloromethane (60 mL). The organic solution was washed with aqueous sodium bicarbonate, dried over magnesium sulfate and concentrated in vacuo to obtain pure product B (1.28 g, 94% yield) as an oil. Note: in large scale, it is desirable to use more excess nitric and sulfuric acid and to carry out the reaction by stirring vigorously with a mechanical stirrer.

¹H NMR (CDCl₃) δ1.49 (t, J=7.0 Hz, 3H), 4.56 (q, J=7.0 Hz, 2H), 7.24 (t, J=8.0 Hz, 1H), 8.3 (m, 1H).

C. 6-Amino-2-fluoro-5-nitrobenzoic acid, ethyl ester

To a solution of compound B (25.0 g, 108 mmol) in ethanol (250 mL) at room temperature was added a solution of ammonium hydroxide (5 mL of 29% solution). Upon addition of ammonium hydroxide, a yellow color developed instantaneously and the solid started to precipitate slowly out of the solution. After 4 hours, additional ammonium hydroxide solution (4 mL) was added and the reaction mixture was stirred overnight. Most of the solvent was removed in vacuo and the residue was triturated with isopropanol. The solid was filtered, washed with water (50 mL) and dried to obtain the desired product C (20.0 g, 81% yield) as a yellow solid.

Melting point: 75°-77° C.

D. 6-Amino-2-ethoxy-5-nitrobenzoic acid, ethyl ester

Sodium hydride (1.48 g, 37.0 mmol, 60% dispersion) was added in small portions to ethanol (50 mL) at ice bath temperature. When the gas evolution ceased, fluoro compound C (6.84 g, 30.0 mmol) was added to the cold ethoxide solution. After 40 minutes, additional ethanol (30 mL) was added because the mixture became too thick to stir. The mixture was warmed to room temperature and stirred for 1 hour. Hydrochloric acid (1N, 45 mL) was added to the reaction mixture and it was stirred for 5 minutes. The precipitated solid was filtered, washed with water and dried to obtain compound D (6.40 g, 84% yield) as a yellow solid.

Melting point: 68°-70° C.

E. 5,6-Diamino-2-ethoxybenzoic acid, ethyl ester

The reduction of nitro compound D (7.80 g, 30.7 mmol) in ethyl acetate was carried out under 50 psi of hydrogen gas in the presence of 5% palladium on carbon (1.2 g) for 3 hours. The catalyst was filtered through a Celite ® bed, washed with chloroform and the filtrate solution was concentrated in vacuo to obtain diamino compound E (6.72 g, 100% yield) as a viscous material. This product was used directly for the next step.

¹H NMR (CDCl₃) δ1.37 (t, J=7.0 Hz, 3H), 1.38 (t, J=7.0 Hz, 3H), 3.95 (q, J=7.0 Hz, 2H), 3.95 (s, broad, 4H), 4.38 (q, J=7.0 Hz, 2H), 6.18 (d, J=8.8 Hz, 1H), 6.71 (d, J=8.8 Hz, 1H).

¹³C NMR (CDCl₃) δ14.3, 14.9, 60.6, 65.1, 102.4, 106.7, 120.7, 126.9, 140.2, 153.6, 168.5.

F. 2-Butyl-6-ethoxy-3-oxo-1,2,4-trihydroquinoxaline-5-carboxylic acid, ethyl ester A mixture of compound E (6.70 g, 29.9 mmol), ethyl 2-bromohexanoate (6.70 g, 30.0 mmol) and sodium bicarbonate (2.6 g) in dimethylformamide (100 mL) was purged with argon gas for a few minutes and heated for 3 hours at 90° C., overnight at 130° C. and 4.5 hours at 145° C. Most of the solvent was removed under reduced pressure and the residue was passed through a flash chromatography column on silica gel eluting with 3:1/hexane:ethyl acetate to obtain product F (7.20 g, 75% yield) as an yellow solid.

Melting point: 68°-70° C.

G. 2-Butyl-6-ethoxy-4-hydro-3-oxoquinoxaline-5-carboxylic acid, ethyl ester

A mixture of compound F (6.50 g, 20.3 mmol) and manganese dioxide (12.0 g) in tetrahydrofuran (60 mL) was heated at reflux temperature overnight. The solid was filtered through a Celite ® bed, washed with ethyl acetate and the filtrate solution was concentrated. The residue was triturated with ether to obtain compound G (5.20 g, 80% yield) as a beige-colored solid.

Melting point: 123°-125° C.

H. 2-Butyl-3-chloro-6-ethoxyquinoxaline-5-carboxylic acid, ethyl ester

A solution of compound G (4.50 g, 14.2 mmol) in phosphorous oxychloride (35 mL) was heated at reflux temperature for 80 minutes. Most of the residual phosphorous oxychloride was removed in vacuo. The residue was dissolved in chloroform (100 mL) and washed with aqueous sodium bicarbonate solution. The organic solution was concentrated and the residue was passed through a flash chromatography column on silica gel eluting with 3:1/hexane:ethyl acetate to obtain product H (4.70 g, 99% yield) as a white solid.

Melting point: 63°-65° C.

I. 2-Butyl-6-ethoxy-3-[[2'-(1H-tetrazol-5-yl)[1,1'-biphenyl]-4-yl]oxy]quinoxaline-5-carboxylic acid, methyl ester A mixture of chloroquinoxaline H (1.00 g, 2.97 mmol), hydroxybiphenyl B from Example 2 (0.71 g, 2.97 mmol) and cesium carbonate (2.00 g) in dimethylformamide (15 mL) was heated at 95° C. overnight. The mixture was directly loaded onto the flash chromatography column on silica gel and eluted with ethyl acetate containing 0.5% acetic acid to provide the product, contaminated by dimethylformamide. After removing dimethylformamide in vacuo, Example 13 (1.12 g, 70% yield) was obtained as a viscous material.

¹H NMR (CDCl₃) δ0.98 (t, J=7.6 Hz, 3H), 1.18 (t, J=7.0 Hz, 3H), 1.43 (t, J=7.0 Hz, 3H), 1.50 (sx, J=7.6 Hz, 2H), 1.84 (qn, J=7.6 Hz, 2H), 3.08(d, J=7.6 Hz, 1H), 3.11 (d, J=7.6 Hz, 1H), 4.19 (q, J=7.0 Hz, 2H), 4.21 (q, J=7.0 Hz, 2H), 7.10-7.96 (m, 10H).

¹³C NMR (CDCl₃) δ13.9, 14.1, 14.7, 22.7, 29.9, 33.2, 61.8, 65.2, 114.4, 122.1, 128.1, 130.0, 130.6, 130.7, 130.9.

EXAMPLE 14

2-Butyl-6-ethoxy-3-[[2'-(1H-tetrazol-5-yl)[1,1'-biphenyl]-4-yl]oxy]quinoxaline-5-carboxylic acid, methyl ester, 1-oxide A mixture of Example 13 (1.13 g, 2.42 mmol) and m-chloroperoxybenzoic acid (1.00 g, 80-85% purity) in chloroform (15 mL) was stirred at room temperature for 3 hours. Thin layer chromatography showed a small amount of starting material left. The reaction mixture was left at about 5° C. for 48 hours. Most of the solvent was removed in vacuo and the residue was passed through a flash chromatography column on silica gel eluting with 0.5% acetic acid in ethyl acetate to obtain the product, which was slightly contaminated by m-chloroperoxybenzoic acid. This material was triturated with a small amount of ethyl acetate to obtain pure Example 14 (505 mg) as a white solid.

Melting point: 133°–136° C.

$^1$H NMR (CD$_3$OD) $\delta$1.10(t, J=7.6 Hz, 3H), 1.17 (t, J=7.0 Hz, 3H), 1.47 (t, J=7.0 Hz, 3H), 1.58 (sx, J=7.6 Hz, 2H), 1.84 (qn, J=7.6 Hz, 2H), 3.29 (d, J=7.6 Hz, 1H), 3.31 (d, J=7.6 Hz, 1H), 4.22 (q, J=7.0 Hz, 2H), 4.24 (q, J=7.0 Hz, 2H), 7.23–7.83 (m, 9H), 8.50 (dd, J$_1$=10.0 Hz, J$_2$=2.3 Hz, 1H).

$^{13}$C NMR (CD$_3$OD) $\delta$14.2, 14.5, 15.0, 23.9, 25.5, 28.4, 62.8, 66.5, 115.7, 122.1, 122.8, 129.1, 130.2, 131.2, 131.8, 132.0, 132.6, 137.4, 139.4, 142.7, 153.7, 158.6, 159.6; MS (M+H)$^+$555, (M+H−O)$^+$539.

Analysis for C$_{30}$H$_{30}$N$_6$O$_5$: Calc'd: C,64.97; H,5.45; N,15.15. Found: C,64.78; H,5.16; N,15.27.

EXAMPLE 15

2-Butyl-6-ethoxy-3-[[2'-(1H-tetrazol-5-yl)[1,1'-biphenyl]-4-yl]oxy]quinoxaline-5-carboxylic acid A. 3-Bromo-2-butyl-6-ethoxyquinoxaline-5-carboxylic acid

Method I

To a solution of chloride H from Example 13 (2.42 g, 7.2 mmol) in methylene chloride (10 mL) at −78° C. was added boron tribromide (14.4 mL of 1M of methylene chloride solution). The mixture was stirred at −78° C. for 6 hours, and the reaction was quenched by adding 5% aqueous citric acid solution (30 mL). The methylene chloride solution was taken, washed with water (30 mL), dried over sodium sulfate, and concentrated. The residue was purified through a flash chromatography column on silica gel eluting with chloroform containing 1% acetic acid to afford bromo compound A (1.27 g) as a solid, which was mixed with chloro quinoxaline derivatives. The isomer ratio is about 1:1 by HPLC (YMC S3-ODS column (6×150 mm) with 78% aqueous methanol as a mobile phase)

Method II

A mixture of compound G from Example 13 (2.11 g, 6.9 mmol), powdered sodium hydroxide solid (1.7 g, 42.5 mmol) and 1,4,7,10,13,16-hexaoxacyclooctadecane ether (200 mg, 0.75 mmol) in toluene (40 mL) was heated at reflux temperature for 4 hours. The reaction mixture was then cooled and the product was extracted with water (2×50 mL). The extracted aqueous solution was acidified with 4N aqueous hydrochloric acid to pH 2. The solid was collected, washed with water and added to obtain 2-butyl-6-ethoxy-3-oxoquinoxaline-5-carboxylic acid, ethyl ester (1.76 g, 92%) as a white solid. It was pure enough for next reaction. The product can be recrystallized from ethanol. Note: good stirring with a mechanical stirrer is desirable.

Melting point: 168°–169° C.

A solution of the above ester (1.4 g, 4.8 mmol) in phosphorus oxychloride (10 mL) was heated at reflux temperature for 1 hour. Most of the excess phosphorus oxychloride was removed under reduced pressure. The residue was poured into ice-water (100 mL). The product was extracted with ethyl acetate (3×20 mL), dried over sodium sulfate and concentrated in vacuo. The residue was chromatographed on silica gel eluting with chloroform containing 1% acetic acid to afford compound A (980 mg, 66%) as a solid.

Melting point: 147°–147.5° C., and the starting material recovered (120 mg).

B. 2-Butyl-6-ethoxy-3-[[2'-(1H-tetrazol-5-yl)[1,1'-biphenyl]-4-yl]oxy]quinoxaline-5-carboxylic acid A mixture of compound A (mixed with chloroquinoxaline derivative, 1.24 g, about 3.75 mmol), biphenyl B from Example 2 (0.98 g, 4.12 mmol) and cesium carbonate (4.02 g, 12.4 mmol) in dimethylformamide (15 mL) was stirred at 70° C. for 5 hours. The reaction mixture was cooled, diluted with water (100 mL) and acidified with 2N aqueous hydrochloric acid. The product was extracted with ethyl acetate (3×40 mL), dried over sodium sulfate and concentrated. The residue was purified by preparative HPLC (column: YMC S-10 ODS, 30×500 mm; mobile phase: 85% methanol in water containing 0.1% trifluoroacetic acid; UV 254 nm; flow rate: 70 mL/min; R$_t$ about 22 minutes) to afford Example 15 (1.65 g, 86%) as a solid.

Melting point: 137°–146° C. R$_f$=0.36 in ethyl acetate containing 1% acetic acid by UV, silica gel plate. HPLC: R$_t$=6.43 minutes at 254 nm, solvent system 78.0% aqueous methanol containing 0.2% phosphoric acid, 1.5 mL/min flow rate in YMC S3-ODS column (6.0×150 mm ).

$^1$H NMR (DMSO) $\delta$8.01 (dd, J=8.2, J=1.2, 1H), 7.77–7.53 (m, 5H), 7.40 (d, J=7.6 Hz, 2H), 7.20 (d, J=7.6 Hz, 2H), 4.25 (q, J=7.0 Hz, 2H), 3.04 (t, J=7.6 Hz, 2H), 1.83 (qn, J=7.6 Hz, 2H), 1.44 (sx, J=7.6 Hz, 2H), 1.34 (t, J=7.0 Hz, 3H), 0.97 (t, J=7.6 Hz, 3H).

$^{13}$C NMR (DMSO) $\delta$166.6, 154.7, 152.1, 148.9, 140.7, 136.2, 135.8, 133.6, 131.2, 130.7, 129.8, 129.5, 127.8, 120.6, 119.6, 115.1, 74.8, 32.3, 28.9, 22.0, 14.7, 13.8; MS (FAB) 511 (M$^+$+1H).

Analysis for C$_{28}$H$_{26}$N$_6$O$_4$. 0.40 H$_2$O: Calc'd: C, 64.95; H, 5.22; N, 16.23; Found: C, 65.16; H, 4.87; N, 16.02.

EXAMPLE 16

2-Butyl-6-ethoxy-3-[2'-(1H-tetrazol-5-yl)[1,1'-biphenyl]-4-yl]oxy]quinoxaline-5-carboxylic acid, 1-oxide A mixture of Example 15 (0.9 g, 1.76 mmol) and m-chloroperoxybenzoic acid (0.6 g, 80~85% content) in methylene chloride (10 mL) was stirred at room temperature for 16 hours. It was concentrated and the residue was chromatographed on silica gel eluting with ethyl acetate containing 1% acetic acid to afford a solid, which was triturated with diisopropyl ether to obtain Example 16 (510 mg, 55%) as a solid.

Melting point: 169°–171° C. R$_f$=0.24, silica gel, 1% acetic acid in ethyl acetate by UV, silica gel plate. R$_t$=4.66 minutes at 254 nm, solvent system 78% aqueous methanol containing 0.2% phosphoric acid, flow rate 1.5 mL/minutes in YMC S3-ODS column (6×150 mm).

$^1$H NMR (CDCl$_3$), $\delta$8.50 (d, J=10 Hz, 1H), 8.00 (d, J=7.2 Hz, 1H), 7.64–7.49 (m, 3H), 7.29 (m, 3H), 7.18 (d, J=8.2 Hz, 2H), 4.28 (q, J=7.6 Hz, 2H), 3.26 (t, J=7.6 Hz, 2H), 1.80 (qn, J=7.6 Hz, 2H), 1.48 (m, 5H), 1.02 (t, J=7.6 Hz, 3H).

$^{13}$C NMR (CDCl$_3$) $\delta$165.5, 161.1, 159.5, 155.0, 152.3, 140.2, 138.5, 137.6, 135.2, 131.3, 131.1, 130.9, 130.6, 129.4, 123.1, 122.8, 115.0, 65.9, 27.3, 24.3, 22.9, 14.6, 13.8; MS(FAB) 527 (M+H)$^+$.

Analysis for $C_{28}H_{26}N_6O_5 \cdot 0.09\ H_2O$: Calc'd: C, 63.67; H, 5.00; N, 15.91; Found: C, 63.60; H, 4.86; N, 15.98.

EXAMPLE 17

2-Butyl-3-[2'-(2H-tetrazol-5-yl)[1,1'-biphenyl]-4-yl-oxy]-5-quinoxolinecarboxylic acid, 2-methyl-1-(1-oxopropoxy)propyl ester, 1-oxide, monosodium salt A. 3-Bromo-2-butylquinoxaline-5-carboxylic acid; and
B. 2-Butyl-3-chloroquinoxaline-5-carboxylic acid To a solution of compound E from Example 15 (1.10 g, 3.95 mmol) in methylene chloride (10 mL) at −78° C. was added a solution of boron tribromide (10 mL of 1M methylene chloride solution). The resulting mixture was then slowly warmed to room temperature and stirred overnight. It was poured into ice-water and the product was extracted with ethyl acetate (2×50 mL), which was washed with 5% aqueous citric acid solution, dried over sodium sulfate and concentrated. The residue was chromatographed on silica gel eluting with hexane/ethyl acetate/acetic acid (12:3:0.01) to afford compound A (1.10 g) as a solid. This compound was found to be mixed with the chloro B derivative in a 3:1 ratio judged by proton NMR.

C. 2-Butyl-3-[[2'-(1H-tetrazol-5-yl)[1,1'-biphenyl]-4-yl]oxy]quinoxaline-5-carboxylic acid A mixture of compound A and B (880 mg, ca. 2.9 mmol), compound B from Example 2 (768 mg, 3.2 mmol) and cesium carbonate (3.15 g, 9.7 mmol) in dimethylformamide (10 mL) was stirred at 80° C. for 8 hours. The reaction mixture was diluted with water (50 mL) and acidified with 1N aqueous hydrochloric acid. The precipitated solid was collected, triturated with ethyl acetate and dried to obtain compound C (1.15 g, 85%) as a white solid.

D. 2-Butyl-3-[2'-(2H-tetrazol-5-yl)[1,1'-biphenyl]-4-yl-oxy]-5-quinoxolinecarboxylic acid, 2-methyl-1-(1-oxopropoxy)propyl ester, 1-oxide; and
E. 2-Butyl-3-[2'-[2-[2-methyl-1-(1-oxopropoxy)propyl]-tetrazol-5-yl][1,1'-biphenyl]-4-yl-oxy]-5-quinoxalinecarboxylic acid A mixture of compound C (1.10 g, 2.36 mmol), silver carbonate (0.65 g, 2.36 mmol) and propanoic acid, 1-chloro-2-methylpropyl ester (0.40 g, 2.43 mmol) in tetrahydrofuran (10 mL) and toluene (10 mL) was stirred at 70° C. for 16 hours. It was cooled to room temperature and treated with 1N of aqueous hydrochloric acid (5 mL). The mixture was filtered through a Celite® pad, which was washed with dimethylformamide (20 mL). The combined filtrate was concentrated in vacuo. The residue was triturated with ethyl acetate and the precipitated solid was collected, which was found to be the starting material (390 mg). The mother liquor was concentrated again and chromatographed on silica gel eluting with hexane/ethyl acetate/acetic acid (2:1:0.01) to obtain compound D (310 mg, 34%) as a foam, and compound E (70.0 mg, 7.7%) as a solid.

Compound D: $^1$H-NMR (CDCl$_3$) δ8.15 (dd, J=1.2 Hz, J=8.2 Hz, 1H), 8.07 (d, J=7.6 Hz, 1H), 7.96 (d, J=7.6 Hz, 1H), 7.65–7.45 (m, 4H), 7.22 (d, J=8.2 Hz, 2H), 7.14 (d, J=8.2 Hz, 2H), 6.91 (d, J=5.3 Hz, 1H), 3.13 (t, J=7.6 Hz, 2H), 2.25 (m, 2H), 2.04 (sx J=7.6 Hz, 1H), 1.89 (qn, J=7.6 Hz, 2H), 1.52 (sx, J=7.6 Hz, 2H), 1.04–0.94 (m, 12H).

$^{13}$C NMR (CDCl$_3$) δ172.9, 163.2, 156.1, 152.6, 151.9, 140.4, 139.3, 137.5, 136.0, 132.6, 131.1, 130.5, 130.0, 127.9, 127.1, 126.1, 123.0, 122.1, 93.0, 33.2, 31.7, 29.5, 27.2, 22.6, 16.4, 16.3, 13.9, 8.6.

Compound E: $^1$H NMR (CDCl$_3$), δ8.60 (dd, J=1.2 Hz, J=7.2 Hz, 1H), 8.25 (dd, J=1.2 Hz, J=8.2 Hz, 1H), 7.92 (d, J=7.2 Hz, 1H), 7.74 (t, J=8.2 Hz, 1H), 7.56 (m, 3H), 7.36 (8.2 Hz, 2H), 7.15 (d, J=8.2 Hz, 2H), 6.84 (d, J=8.8 Hz, 1H), 3.23 (t, J=7.6 Hz, 2H), 2.56 (sx, J=8.2 Hz, 1H), 2.39 (m, 2H), 1.96 (qn, J=7.6 Hz, 2H), 1.57 (sx, J=7.6 Hz, 2H), 1.15–0.99 (m, 9H), 0.73 (d, 7.0 Hz, 3H).

$^{13}$C NMR (CDCl$_3$) δ172.2, 165.7, 165.0, 155.2, 150.6, 140.7, 139.9, 138.9, 136.1, 134.5, 133.6, 131.3, 130.3, 130.2, 127.9, 127.4, 125.8, 123.1, 120.8, 86.7, 33.2, 32.1, 29.4, 27.0, 22.6, 17.4, 17.1, 13.8, 8.6.

F. 2-Butyl-3-[2'-(2H-tetrazol-5-yl)[1,1'-biphenyl]4-yl-oxy]quinoxoline-5-carboxylic acid, 2-methyl -1-(1-oxopropoxy)propyl ester, 1-oxide, monosodium salt A mixture of compound D (300 mg, 0.5 mmol) and m-chloroperoxybenzoic acid (110 mg, 80–85% content) in methylene chloride (2 mL) was stirred at room temperature overnight. The mixture was concentrated and chromatographed on silica gel eluting with hexane/ethyl acetate/acetic acid (2:1:0.01 ) to afford the desired compound (290 mg, 94%) as a gel. The compound was dissolved in methanol and treated with 0.5 mL of 1M aqueous sodium bicarbonate solution. The resulting solution was concentrated in vacuo, and the residue was passed through a column on HP-20, eluting with water followed by 50% to 70% methanol in water. The desired fractions were pooled, mostly concentrated and lyophilized to afford Example 17 (140 mg, 44%) as a solid.

Melting point: 135°–138° C. (It might be better to elute the column with 80–90% methanol to obtain better recovery). $R_f$=0.32 in ethyl acetate/hexane (50:50) containing 1% acetic acid by UV, silica gel plate. HPLC: $R_t$=15.6 minutes at 254 nm, solvent system 78.0% aqueous methanol containing 0.2% phosphoric acid, 1.5 mL/minute flow rate in YMC S3-ODS column (6.0×150 mm).

$^1$H NMR (CD$_3$OD) δ8.17 (dd, J=1.2 Hz, J=8.2 Hz, 1H), 7.51 (dd, J=1.2 Hz, J=7.6 Hz, 1H), 7.27–7.02 (m, 5H), 6.77 (s, 4H), 6.24 (d, J=5.2 Hz, 1H), 2.87 (t, J=7.6 Hz, 2H), 1.85 (q, J=7.6 Hz, 2H), 1.37 (m, 3H), 1.08 (sx, J=7.6 Hz, 2H), 0.62 (m, 6H), 0.34 (m, 6H).

$^{13}$C NMR (CD$_3$OD) δ174.4, 166.3, 162.8, 159.5, 153.1, 142.4, 139.8, 136.1, 132.8, 132.0, 131.8, 131.5, 130.0, 128.2, 128.1, 123.0, 121.7, 95.4, 32.8, 28.2, 28.1, 25.8, 23.9, 17.1, 16.8, 14.2, 9.2; MS(FAB) 655 (M+2Na−H)$^+$, 633 (M+Na)$^+$, 617 (M+Na−O)$^+$.

Analysis for $C_{33}H_{33}N_6O_6Na \cdot 1.07\ H_2O$: Calc'd: C, 60.80; H, 5.43; N, 12.89. Found: C, 60.66; H, 4.94; N, 13.03.

EXAMPLE 18

2-Butyl-6-ethoxy-3-[[2'-(1H-tetrazol-5-yl)[1,1'-biphenyl]-4-yl]oxy]quinoxaline-5-carboxylic acid, 2-methyl-1-(1-oxopropoxy)propyl ester A. 1-Chloro-2-methylpropyl propanoate To freshly fused zinc chloride (41 mg) in methylene chloride (10 mL) was added propionyl chloride (5.0 g, 54.0 mmol). The reaction was cooled to 10° C. and isobutyraldehyde (3.89 g, 54.0 mmol) was added dropwise maintaining the temperature at 25° C. Once the addition was complete, the reaction was stirred for one hour at room temperature. The reaction mixture was washed with 20% sodium acetate and the organic phase was concentrated in vacuo to provide compound A.

B. 2-Butyl-6-ethoxy-3-[[2'-(1H-tetrazol-5-yl)[1,1'-biphenyl]-4-yl]oxy]quinoxaline-5-carboxylic acid, 2-methyl-1-(1-oxopropoxy)propyl ester A mixture of Example 15 (650 mg, 1.27 mmol), silver oxide (1.50 g, 6.47 mmol) and activated 4A molecular sieves powder (1.0 g) in tetrahydrofuran (10 mL) was stirred for 5 minutes at room temperature. To this mixture was added chloro compound A (190 mL) and the reaction mixture was heated at 65° C. After 1.5 hours, an additional 300 mL of chloro compound A was added and continued to heat at 65° C. for 6 hours. An additional 300 mL of chloro compound A was added and the mixture was heated at 62°-65° C. overnight. Ethyl acetate (150 mL) and aqueous hydrochloric acid (30 mL of 1N solution) were then added to the reaction mixture, and it was stirred for a few minutes. It was filtered through a Celite® bed and washed with ethyl acetate, and the organic layer was taken from the filtrate solution. The aqueous layer was washed with ethyl acetate (30 mL) and the combined organic solution was dried over magnesium sulfate, concentrated and the residue was purified by preparative silica gel thin layer chromatography using a solvent system of hexane: ethyl acetate: ethanol (300:100:50) to obtain Example 18 (380 mg, 47%) as a glassy material.

$^1$H NMR (CDCl$_3$) δ0.85-1.55 (m, 16H), 1.84 (qn, J=7.6 Hz, 2H), 2.05 (sx, J=7.6 Hz, 2H), 2.30 (q, J=7.6 Hz, 2H), 3.05 (t, J=7.6 Hz, 2H, looks like 2 doublets), 4.20 (m, 2H, looks like two quartets), 6.94 (d, J=5.3 Hz, 1H), 7.15-8.00 (m, 10H).

$^{13}$C NMR (CDCl$_3$) d 8.8, 13.9, 14.7, 16.0, 16.5, 22.6, 27.4, 29.8, 31.5, 33.1, 65.1, 93.3, 114.0, 117.0, 121.7, 123.0, 127.9, 130.0, 130.7, 131.0, 134.0, 135.9, 137.5, 140.5, 149.5, 152.4, 155.8, 156.1, 164.3, 173.1.

EXAMPLE 19

2-Butyl-6-ethoxy-3-[[2'-(1H-tetrazol-5-yl)[1,1'-biphenyl]-4-yl]oxy]quinoxaline-5-carboxylic acid, 2-methyl-1-(1oxopropoxy)propyl ester, 1-oxide A mixture of Example 18 (385 mg, 0.60 mmol) and m-chloroperoxybenzoic acid (165 mg, 80-85% purity) in dichloromethane (5 mL) was stirred at room temperature overnight. The solid was filtered and the filtrate solution was directly passed through a preparative HPLC column to obtain (179 mg, 45%) as a white hydrated solid.

Melting point: 80°-85° C. Preparative HPLC condition:YMC S-10 ODS 30×500 mm column, 80% methanol in water containing 0.1% trifluoroacetic acid, 35 mL/min. flow rate, 254 nm, Rt=about 35 minutes.

$^1$H NMR (CD$_3$OD) δ0.83 (t, J=7.6 Hz, 6H, looks like two doublets), 1.09 (t, J=7.6 Hz, 3H), 1.16 (t, J=7.6 Hz, 3H), 1.48 (t, J=6.4 Hz, 3H), 1.58 (sx, J=8.0 Hz, 2H), 1.85 (m, 3H, qn for 2H+hep for 1H), 2.40 (q, J=7.6 Hz, 2H, looks like two quartets), 3.30 (t, J=7.6 Hz, 2H), 4.34 (q, J=7.0 Hz, 2H), 6.79 (d, J=4.7 Hz, 1H), 7.32 (q, J=6.5 Hz, 4H), 7.55 (d, J=9.4Hz, 1H), 7.68-7.84 (m, 4H), 8.53 (d, J=9.4 Hz, 1H).

$^{13}$C NMR (CD$_3$OD) δ9.2, 15.1, 16.5, 17.0, 23.9, 24.2, 25.5, 28.2, 28.4, 32.7, 66.6, 94.6, 115.6, 119.5, 122.4, 122.5, 124.3, 129.1, 130.3, 131.3, 131.8, 132.1, 132.6, 137.6, 137.8, 139.3, 142.6, 153.7, 158.8, 159.6, 165.3, 173.8; MS (M+H)+655, (M+H−O)+639.

Analysis for C$_{35}$H$_{38}$N$_6$O$_7$.0.69H$_2$O: Calc'd: C,63.00; H,5.95; N,12.60. Found: C,63.06; H,5.69; N,12.54.

EXAMPLE 20

2-Butyl-6-(1-methylethoxy)-3-[[2'-(1H-tetrazol-5-yl)[1,1'biphenyl]-4-yl]oxy]quinoxaline-5-carboxylic acid.

A. 2-Amino-6-(1-methylethoxy)-3-nitrobenzoic acid, 1-methylethyl ester

To isopropyl alcohol (60 mL) at 0° C. was added in portions sodium hydride (1.25 g, 60% content in an oil). The mixture became very viscous. When the gas evolution ceased, fluoro compound C from Example 13 (2.37 g, 10.4 mmol) was added. The resulting mixture soon turned red. It was stirred at room temperature for 3 hours and acidified with 1N aqueous hydrochloric acid (25 mL). Most of the solvent was removed under reduced pressure. The residue was partitioned between ethyl acetate (50 mL) and brine, the organic layer was taken, dried over sodium sulfate, concentrated and chromatographed on silica gel eluting with hexane/ethyl acetate (6:1) to afford compound A (2.3 g, 78%) as an yellow oil.

$^1$H NMR (CDCl$_3$) δ8.24 (d, J=9.4 Hz, 1H), 7.57 (broad, 2H), 6.30 (d, J=9.4 Hz, 1H), 5.28 (sp. J=5.9 Hz, 1H), 4.72 (sp, J=5.9 Hz, 1H), 1.37 (d, J=5.9 Hz, 6H), 1.36 (d, J=5.9 Hz, 6H).

$^{13}$C NMR (CDCl$_3$) δ166.8, 163.6, 147.1, 131.1, 126.8, 106.7, 102.1, 71.7, 68.9, 22.0, 21.8.

B. 2,3-Diamino-6-(1-methylethoxy)benzoic acid, 1-methylethyl ester

Compound A (2.3 g, 8.16 mmol) in ethyl acetate (20 mL) and ethanol (20 mL) was reduced under 50 psi. of H$_2$ in the presence of palladium on charcoal (500 mg, 5% content) overnight. The catalyst was filtered through a Celite® pad. The filtrate was concentrated to afford compound B (2.05 g, 100%) as an oil, which was used directly for the next step due to its susceptibility to air oxidation.

$^1$H NMR (CDCl$_3$) δ6.68 (d, J=8.8 Hz, 1H), 6.18 (d, J=8.2 Hz, 1H), 5.26 (sp, J=6.4 Hz, 1H), 4.41 (sp, J=6.4 Hz, 1H), 4.24 (broad, 4H), 1.35 (d, J=6.4 Hz, 6H), 1.27 (d, J=6.4 Hz, 6H);

$^{13}$C NMR (CDCl$_3$) δ168.0, 151.7, 139.1, 126.4, 120.3, 111.8, 104.3, 71.2, 68.0, 22.0, 21.8.

C. 2-Butyl-6-(1-methylethoxy)-3-oxo-1,2,4-trihydro-5-quinoxalinecarboxylic acid, 1-methylethyl ester A mixture of compound B (2.0 g, 7.9 mmol), ethyl 2-bromohexanoate (2.0 g, 9 mmol) and sodium hydrogen carbonate (0.84 g, 10 mmol) in dimethylformamide (5 mL) was stirred at 120° C. for 3 hours and then at 140°-145° C. for 3 hours. The mixture was cooled to room temperature and diluted with ethyl acetate (50 mL). It was filtered and the filtrate was concentrated. The residue was purified through a flash chromatography column on silica gel eluting with hexane/ethyl acetate (4:1) to afford compound C (1.75 g, 64%) as a solid.

Melting point: 102°-103° C.

D. 2-Butyl-4-hydro-6-(1-methylethoxy)-5-quinoxalinecarboxylic acid, 1-methylethyl ester A mixture of compound C (1.70 g, 4.9 mmol) and manganese dioxide (3.5 g, 40 mmol) in tetrahydrofuran (10 mL) was stirred at reflux temperature for 4 hours. The mixture was cooled to room temperature and filtered through a Celite® pad, washed with ethyl acetate, and the filtrate was concentrated to afford compound D (1.53 g, 90%) as a solid. This material was pure enough for the next step.

Melting point: 77°–78° C.

E. 2-Butyl-4-hydro-6-(1-methylethoxy)-5-quinoxalinecarboxylic acid

A mixture of compound D (1.5 g, 4.3 mmol), powdered sodium hydroxide (1.08 g, 27 mmol) and 1,4,7,10,13,16-hexaoxacyclooctadecane ether (240 mg, 0.9 mmol) in toluene (10 mL) was stirred vigorously at reflux temperature for 4 hours. The reaction mixture was then cooled to room temperature and the product was extracted with water (3×30 mL). The aqueous solution was decolorized with active charcoal and acidified to pH 3 with 4N aqueous hydrochloric acid to precipitate compound E, which was collected, washed with water and dried to obtain solid product (1.01 g, 77%).

Melting point: 162°–163° C.

F. 2-Butyl-3-chloro-6-(1-methylethoxy)-5-quinoxalinecarboxylic acid

A suspension of compound E (0.90 g, 2.96 mmol) in phosphorus oxychloride (10 mL) was stirred at reflux temperature. It soon became a homogeneous solution and the solution was refluxed for 1 hour. Most of the excess phosphorus oxychloride was removed under reduced pressure. The residue (about 50 g) was poured onto ice. The mixture was extracted with ethyl acetate (3×20 mL), dried over sodium sulfate and concentrated. The residue was purified through a flash chromatography column on silica gel eluting with hexane/ethyl acetate/acetic acid (50:50:1) to afford compound F (0.83 g, 87%) as a solid.

Melting point: 113°–114° C.

G. 2-Butyl-6-(1-methylethoxy)-3-[[2'-(1H-tetrazol-5-yl)-[1,1'-biphenyl]-4-yl]oxy]quinoxaline-5-carboxylic acid A mixture of compound F (0.76 g, 2.36 mmol), hydroxybiphenyl B from Example 2 (0.59 g, 2.48 mmol) and cesium carbonate (2.42 g, 7.45 mmol) in dimethylformamide (10 mL) was stirred at 70° C. overnight. The mixture was cooled to room temperature and diluted with ethyl acetate (100 mL). Water (50 mL) was added to the mixture and the solution was adjusted to pH 3 with 1N aqueous hydrochloric acid. The organic solution was taken, washed with brine, dried over sodium sulfate and concentrated. The residue was chromatographed on silica gel eluting with hexane/ethyl acetate/acetic acid (1:1:0.01 ) to afford Example 20 (0.91 g, 73%) as a foam.

$^1$H NMR (CDCl$_3$) δ8.15 (d, J=9.4 Hz, 1H), 7.96 (d, J=7.0 Hz, 1H), 7.57 (m, 3H), 7.46 (d, J=9.4 Hz, 1H), 7.33 (d, J=8.8 Hz, 2H), 7.23 (d, J=8.8 Hz, 2H), 4.85 (sp, J=5.9 Hz, 1H), 3.23 (t, J=7.6 Hz, 2H), 1.98 (qn, J=7.6 Hz, 2H), 1.59 (sx, J=7.6 Hz, 2H), 1.47 (d, J=5.9 Hz, 6H), 1.09 (t, J=7.6 Hz, 3H).

$^{13}$C NMR (CDCl$_3$) δ166.2, 159.9, 156.0, 155.1, 152.1, 148.6, 140.2, 137.3, 133.7, 132.4, 131.1, 130.9, 130.8, 130.5, 128.2, 122.8, 122.4, 117.5, 113.0, 73.2, 32.6, 29.7, 22.5, 22.0, 20.7, 13.8.

EXAMPLE 21

2-Butyl-6-(1-methylethoxy)-3-[[2'-(1H-tetrazol-5-yl)[1,1'-biphenyl]-4-yl]oxy]quinoxaline-5-carboxylic acid, 1-oxide A mixture of Example 20 (250 mg, 0.48 mmol) and m-chloroperoxybenzoic acid (250 mg, 80–85% content) in methylene chloride (3 mL) was stirred at room temperature overnight. The mixture was filtered and the filtrate was concentrated. The residue was purified by preparative HPLC (column: YMC S-10 ODS 30×500 mm; flow rate: 30 mL/min; solvent system: 78% methanol containing 0.1% trifluoroacetic acid; UV 254 nm) to afford Example 21 (210 mg, 81%) as a solid.

Melting point: 134°–136° C. R$_f$=0.18 in ethyl acetate containing 1% acetic acid. R$_t$=5.56 minutes at 254 nm, solvent system 78% aqueous methanol containing 0.2% phosphoric acid, 1.5% mL/min flow rate in YMC S3-ODS column (6.0×150 mm).

$^1$H NMR (CDCl$_3$) δ11.25 (br.s, 2H), 8.42 (d, J=9.4 Hz, 1H), 7.89 (d, J=7.6 Hz, 1H), 7.42 (m, 3H), 7.18 (m, 3H), 7.07 (d, J=8.8 Hz, 2H), 4.69 (sp, J=5.8 Hz, 1H), 3.17 (t, J=7.6 Hz, 2H), 1.71 (qn, J=7.6 Hz, 2H), 1.43 (sx, J=7.6 Hz, 2H), 1.31 (d, J=5.8 Hz, 6H), 0.93 (t, J=7.6 Hz, 3H).

$^{13}$C NMR (CDCl$_3$) δ166.3, 159.8, 159.3, 155.0, 152.3, 140.3, 138.6, 137.3, 135.3, 131.3, 130.9, 130.7, 130.6, 129.4, 128.4, 122.7, 116.5, 115.5, 73.2, 27.3, 24.3, 22.8, 22.0, 13.8; MS (FAB) 541 (M+H)$^+$.

Analysis for C$_{29}$H$_{28}$N$_6$O$_5$.1.03 H$_2$O: Calc'd: C, 62.29; H, 5.42; N, 15.03; Found: C, 62.55; H, 5.14; N, 14.77.

EXAMPLE 22

2-Butyl-6-(1-methylethoxy)-3-[[2'-(1H-tetrazol-5-yl)[1,1'-biphenyl]-4-yl]oxy]quinoxaline-5-carboxylic acid, 2-methyl-1-(1-oxopropoxy)propyl ester A mixture of Example 20 (0.63 g, 1.2 mmol) and silver oxide (1.20 g, 5.2 mmol) in tetrahydrofuran (6 mL) was stirred in the presence of molecular sieves (1.2 g, 4 Å powder) at 65° C. for 10 minutes. To this mixture was added compound chloro compound A from Example 18 (0.7 mL) and it was stirred at 65° C. overnight. To the mixture were added ethyl acetate (20 mL), 2N aqueous hydrochloric acid (5 mL) and brine (10 mL), and it was stirred for 5 minutes. The solid was filtered through a Celite ® pad, and the pad was washed with ethyl acetate (20 mL). The filtrate solution was washed with brine, dried over sodium sulfate and concentrated. The crude product was dissolved in methanol (10 mL) and 5% aqueous sodium hydrogen carbonate (2.5 mL), and the mixture was stirred at room temperature for 5 hours and stored in a refrigerator overnight. Most of the methanol was removed under reduced pressure. The residue was acidified with 2N aqueous hydrochloric acid to pH 4 and partitioned between ethyl acetate (20 mL) and brine. The organic layer was taken, dried over sodium sulfate and concentrated in vacuo. The residue was chromatographed on silica gel eluting with hexane/ethyl acetate/acetic acid (2:1:0.01) to afford Example 22 (0.53 g, 87%) as an oil and the dialkylated compound (0.22 g).

$^1$H NMR (CDCl$_3$) δ7.83 (d, J=8.8 Hz, 1H), 7.80 (d, J=7.0 Hz, 1H), 7.48–7.33 (m, 3H), 7.04 (m, 5H), 6.84 (d, J=4.7 Hz, 1H), 4.62 (J=5.8 Hz, 1H), 2.94 (t, J=7.1 Hz, 2H), 2.19 (q, J=7.6 Hz, 2H), 1.92 (ot, J=5.1 Hz, 1H), 1.72 (qn, J=7.1 Hz, 2H), 1.37 (sx, J=7.1 Hz, 2H), 1.26 (d, J=5.8 Hz, 3H), 1.23 (d, J=5.8 Hz, 3H), 1.00–0.77 (m, 12H).

$^{13}$C NMR (CDCl$_3$) δ173.0, 164.3, 155.6, 155.1, 152.2, 149.3, 140.6, 135.8, 133.9, 130.9, 130.8, 130.6, 130.3, 129.9, 128.0, 123.2, 121.4, 118.3, 115.4, 93.1, 71.9, 33.0, 31.5, 29.7, 27.3, 22.5, 21.9, 16.4, 15.9, 13.8, 8.7.

Example 23

2-Butyl-6-(1-methylethoxy)-3-[[2'-(1H-tetrazol-5-yl)[1,1'-biphenyl]-4-yl]oxy]quinoxaline-5-carboxylic acid, 2-methyl-1-(1-oxopropoxy)propyl ester, 1-oxide A mixture of Example 22 (0.5 g, 0.77 mmol) and m-chloroperoxybenzoic acid (0.61 g, 80–85% content) in methylene chloride (10 mL) was stirred at room temperature for 4 hours. The solid was then filtered and the filtrate solution was passed through a flash chromatography column on silica gel eluting with hexane/ethyl acetate/acetic acid (2:1:0.01) to afford Example 23 (0.35 g, 69%), which was dissolved in methanol and water to lyophilyze to obtain a white solid product.

Melting point: 86°–90° C. $R_f$=0.34 in 1% acetic acid in hexane-ethyl acetate (50/50), silica gel plate. $R_t$=12.0 minutes at 254 nm, solvent system 82% aqueous methanol containing 0.2% phosphoric acid, 1.5 % mL/minute flow rate in YMC S3-ODS column (6.0×150 mm).

$^1$H NMR (CDCl$_3$) δ8.39 (d, J=9.4 Hz, 1H), 7.88 (d, J=7.6 Hz, 1H), 7.54–7.39 (m, 3H), 7.19 (d, J=9.4 Hz, 1H), 7.11 (s, 4H), 6.84 (d, J=4.7 Hz, 1H), 4.69 (sp, J=6.4 Hz, 1H), 3.11 (t, J=7.6 Hz, 2H), 2.23 (q, J=7.6 Hz, 2H), 1.95 (ot, J=5.3 Hz, 1H), 1.65 (qn, J=7.6 Hz, 2H), 1.40 (sx, J=7.6 Hz, 2H), 1.30 (d, J=6.4 Hz, 3H), 1.27 (d, J=6.4 Hz, 3H), 0.99–0.80 (m, 12H).

$^{13}$C NMR (CDCl$_3$) δ173.4, 163.8, 158.6, 156.9, 152.4, 140.7, 138.6, 136.5, 136.1, 131.2, 131.0, 130.3, 129.5, 128.2, 123.4, 121.9, 121.8, 119.4, 115.3, 93.5, 72.4, 31.8, 27.6, 24.7, 23.1, 22.2, 16.8, 16.2, 14.0, 9.0; MS 669 (M+H)$^+$, 653 (M+H−O)$^+$.

Analysis for C$_{36}$H$_{40}$N$_6$O$_7$: Calc'd: C, 64.66; H, 6.03; N, 12.57; Found: C, 64.87; H, 5.99; N, 12.42.

EXAMPLE 24

6-(Butoxy)-2-butyl-3-[[2'-(1H-tetrazol-5-yl)[1,1'-biphenyl]-4-yl]oxy]quinoxaline-5-carboxylic acid A. 2-Amino-6-(butoxy)-3-nitrobenzoic acid, butyl ester Sodium metal (1.51 g, 0.066 mol) was added to n-butanol (100 mL) and the mixture was refluxed until all the sodium was consumed. To this solution was added fluoro compound C from Example 13 (5.0 g, 0.022 mol). The resulting mixture was stirred at room temperature for 1 hour and acidified with 4N aqueous hydrochloric acid (12 mL). Most of the solvent was removed under reduced pressure. The residue was partitioned between ethyl acetate (100 mL) and brine, the organic layer was taken, dried over sodium sulfate, concentrated and flash-chromatographed on silica gel eluting with hexane/ethyl acetate (4:1) to afford compound A (4.6 g, 67%) as a yellow oil.

$^1$H NMR (CDCl$_3$) δ8.12 (d, J=10.0 Hz, 1H), 7.68 (broad, 2H), 6.15 (d, J=10.0 Hz, 1H), 4.21 (t, J=6.5 Hz, 2H), 3.95 (t, J=6.4 Hz, 2H), 1.67 (m, 4H), 1.37 (m, 4H), 0.87 (t, J=7.7 Hz, 6H).

$^{13}$C NMR (CDCl$_3$) δ167.2, 164.8, 147.3, 131.4, 125.0, 104.9, 100.9, 69.0, 65.0, 30.8, 30.5, 21.2, 19.0, 18.9, 13.5.

B. 6-(Butoxy)-2,3-diaminobenzoic acid, butyl ester

Compound A (4.6 g, 14.8 mmol) in ethanol (20 mL) was reduced under 50 psi. of H$_2$ in the presence of palladium on charcoal (1 g, 10% content) for 3 hours. The catalyst was filtered through a Celite® pad. The filtrate was concentrated to afford compound B (3.85 g, 93%) as an oil, which was used directly for the next step due to its susceptibility to air oxidation.

$^1$H NMR (CDCl$_3$) δ6.71 (d, J=8.8 Hz, 1H), 6.17 (d, J=8.8 Hz, 1H), 4.95 (broad, 2H), 4.31 (t, J=6.5 Hz, 2H), 3.89 (d, J=6.5 Hz, 2H), 3.03 (br s, 2H), 1.73 (m, 4H), 1.46 (m, 4H), 0.96 (m, 6H).

$^{13}$C NMR (CDCl$_3$) δ168.7, 153.7, 140.2, 126.8, 120.7, 106.8, 101.7, 68.9, 64.6, 31.4, 30.8, 19.2, 13.8, 13.7.

C. 6-(Butoxy)-2-butyl-3-oxo-1,2,4-trihydro-5-quinoxalinecarboxylic acid, butyl ester A mixture of compound B (3.8 g, 13.6 mmol), ethyl 2bromohexanoate (3.4 g, 15 mmol) and sodium hydrogen carbonate (1.26 g, 15 mmol) in dimethylformamide (10 mL) was stirred at 120° C. for 2 hours and then at 140°–145° C. for 6 hours. The mixture was cooled to room temperature and partitioned between ethyl acetate (50 mL) and water (100 mL). The organic layer was taken, washed with brine (50 mL), dried over sodium sulfate and concentrated. The residue was purified through a flash chromatography column on silica gel eluting with hexane/ethyl acetate (6:1) to afford compound C (4.5 g, 88%) as an oil.

$^1$H NMR (CDCl$_3$) δ9.51 (s, 1H), 6.75 (d, J=8.2 Hz, 1H), 6.52 (d, J=8.2 Hz, 1H), 4.32 (t, J=6.4 Hz, 2H), 3.92 (t, J=6.4 Hz, 2H), 3.91 (s, 1H), 3.75 (m, 1H), 1.74 (m, 6H), 1.46 (m, 6H), 0.96 (m, 9H).

$^{13}$C NMR (CDCl$_3$) δ168.6, 167.2, 152.4, 127.7, 127.0, 117.7, 107.8, 107.1, 69.4, 65.3, 56.0, 31.4, 30.9, 30.6, 27.4, 22.4, 19.1, 13.8, 13.7, 13.6.

D. 6-(Butoxy)-2-butyl-4-hydro-3-oxo-5-quinoxalinecarboxylic acid, butyl ester

A mixture of compound C (4.5 g, 12 mmol) and manganese dioxide (9.0 g, 10.3 mmol) in tetrahydrofuran (50 mL) was stirred at reflux temperature for 3 hours. The mixture was cooled to room temperature, diluted with ethyl acetate (50 mL), and filtered through a Celite® pad. The pad was washed with ethyl acetate and the combined filtrate was concentrated to afford compound D (4.1 g, 91%) as a solid. This material was pure enough for the next step.

Melting point: 90°–91° C.

E. 6-(Butoxy)-2-butyl-4-hydro-3-oxo-5-quinoxalinecarboxylic acid

A mixture of compound D (4.0 g, 10.7 mmol), powdered sodium hydroxide (2.57 g, 64.0 mmol) and 1,4,7,10,13,16-hexaoxacyclooctadecane ether (300.0 mg, 1.14 mmol) in toluene (50 mL) was stirred vigorously at reflux temperature for 6 hours. The reaction mixture was then cooled to room temperature and the product was extracted with water (3×30 mL). The aqueous solution was acidified to pH 3 with concentrated hydrochloric acid to precipitate compound E, which was collected, washed with water and dried (2.98 g, 77%).

Melting point: 169°–171° C.

F. 6-(Butoxy)-2-butyl-3-chloro-5-quinoxalinecarboxylic acid

A suspension of compound E (2.63 g, 8.3 mmol) in phosphorus oxychloride (20 mL) was stirred at reflux temperature. It soon became a homogeneous solution and was refluxed for 2 hours. Most of the excess phosphorus oxychloride was removed under reduced pressure. The residue (about 150 g) was poured onto ice. The mixture was extracted with ethyl acetate (3×50 mL), and the extract was dried over sodium sulfate and concentrated. The residue was purified through a flash chromatography column on silica gel eluting with hexane/ethyl acetate/acetic acid (100:100:1) to afford compound F (1.33 g, 53%) as a solid.

Melting point: 139°–140° C.

G. 6-(Butoxy)-2-butyl-3-[[2'-(1H-tetrazol-5-yl)[1,1'-biphenyl]-4-yl]oxy]quinoxaline-5-carboxylic acid A mixture of compound F (0.88 g, 2.6 mmol), biphenyl B from Example 2 (0.65 g, 2.75 mmol) and cesium carbonate (2.68 g, 8.2 mmol) in dimethylformamide (10 mL) was stirred at 70° C. for 8 hours. The mixture was cooled to room temperature and to this mixture was added 8 mL of 2N aqueous hydrochloric acid. The mixture was partitioned between ethyl acetate (50 mL) and water (50 mL). The organic solution was taken, washed with brine, dried over sodium sulfate and concentrated. The residue was purified by preparative HPLC (column: YMC S-10 ODS 3×500 mm; flow rate: 30 mL/min; solvent system: 82% methanol containing 0.1% trifluoroacetic acid; UV 254 nm) to afford Example 24 (0.51 g, 36%) as a foam.

$^1$H NMR (CDCl$_3$) δ8.10(d, J=9.4 Hz, 1H), 7.98 (dd, J=1.7, 8.4 Hz, 1H), 7.60–7.49 (m, 3H), 7.42 (d, J=9.4 Hz, 1H), 7.32 (d, J=8.8 Hz, 2H), 7.17 (d, J=8.8 Hz, 2H), 4.22 (t, J=6.4 Hz, 2H), 3.17 (t, J=7.6 Hz, 2H), 1.88 (m, 4H), 1.54 (m, 4H), 1.03 (t, J=7.6 Hz, 3H), 0.95 (t, J=7.6 Hz, 3H).

$^{13}$C NMR (CDCl$_3$) δ165.4, 161.1, 155.6, 154.9, 151.7, 148.3, 140.7, 137.3, 133.3, 132.8, 130.9, 130.8, 130.6, 130.4, 127.9, 122.6, 122.1, 115.6, 110.6, 69.6, 32.5, 30.8, 29.4, 22.4, 18.8, 13.7, 13.5.

EXAMPLE 25

6-(Butoxy)-2-butyl-3-[[2'-(1H-tetrazol-5-yl)[1,1'-biphenyl]-4-yl]oxy]quinoxaline-5-carboxylic acid, 1-oxide A mixture of Example 24 (0.5 g, 0.93 mmol) and m-chloroperoxybenzoic acid (0.96 g, 80–85% content) in methylene chloride (5 mL) was stirred at room temperature overnight. The mixture was filtered and the filtrate was concentrated. The residue was purified by preparative HPLC (column: YMC S-10 ODS 30×500 mm; flow rate:30 mL/minute; solvent system: 78% methanol containing 0.1% trifluoroacetic acid; UV 254 nm) to afford Example 25 (0.24 g, 47%) as a solid.

Melting point: 120°–122° C. R$_f$=0.37 in ethyl acetate containing 1% acetic acid, silica gel plate. R$_t$=6.91 minute at 254 nm, solvent system 78% aqueous methanol containing 0.2% phosphoric acid, 1.5% m/minute flow rate in YMC S3-ODS column (6.0×150 mm).

$^1$H NMR (CDCl$_3$) δ8.55 (d, J=9.4 Hz, 1H), 8.10 (d, J=8.0 Hz, 1H), 7.58 (m, 3H), 7.34 (m, 3H), 7.19 (d, J=8.8 Hz, 2H), 4.22 (t, J=7.4 Hz, 2H), 3.27 (t, J=7.6 Hz, 2H), 1.84 (m, 4H), 1.54 (m, 4H), 1.02 (t, J=7.6 Hz, 3H), 0.96 (t, J=7.6 Hz, 3H).

$^{13}$C NMR (CDCl$_3$) δ165.3, 161.4, 160.7, 159.6, 154.9, 151.5, 140.1, 138.5, 137.6, 135.2, 131.5, 131.2, 130.9, 130.6, 129.5, 128.6, 123.3, 123.1, 122.8, 115.0, 69.9, 31.0, 27.4, 24.3, 22.9, 19.0, 13.8, 13.7. MS 555 (M+H)$^+$.

Analysis for C$_{30}$H$_{30}$N$_6$O$_5$.0.29 H$_2$O: Calc'd: C, 64.36; H, 5.51; N, 15.01; Found: C, 64.63; H, 5.36; N, 14.74.

EXAMPLE 26

2-Butyl-6-(2,2,2-trifluoroethoxy)-3-[[2'-(1H-tetrazol-5-yl)[1,1'-biphenyl]-4-yl]oxy]quinoxaline-5-carboxylic acid A. 2-Amino-3-nitro-6-(2,2,2-trifluoroethoxy)benzoic acid, ethyl ester To 2,2,2-trifluoroethanol (30 g, 0.3 mmol) in tetrahydrofuran (50 mL) at 0° C. was added in portions sodium hydride (4.2 g, 60% content in an oil). When the gas evolution ceased, fluoro compound C from Example 13 (10.0 g, 44 mmol) was added. The resulting mixture soon turned red. It was stirred at 0° C. for 30 minutes and at room temperature for 20 minutes. To this mixture was added 20 mL of 6N aqueous hydrochloric acid, and most of the solvent was removed under reduced pressure. The residue was mixed with water and the solid was collected, washed with water and then hexane. It was dried to afford compound A (13.95 g, 100%) as a solid.

Melting point: 73°–74° C.

B. 2,3-Diamino-6-(2,2,2-trifluoroethoxy)benzoic acid, ethyl ester

Compound A (13.9 g, 45 mmol) in ethyl acetate (100 mL) and ethanol (100 mL) was reduced under 50 psi. of H$_2$ in the presence of Pd/C (2 g, 5% content) for overnight. The catalyst was filtered through a celite pad. The filtrate was concentrated to afford compound B (12.0 g) as a solid. Compound B was used directly in the next step without physical characterization.

C. 2-Butyl-3-oxo-6-(2,2,2-trifluoroethoxy)-1,2,4-trihydro-5-quinoxalinecarboxylic acid, ethyl ester Compound B (12.0 g, 43.2 mmol) was mixed with ethyl 2-bromo hexanoate (10.6 g, 47.5 mmol) and sodium hydrogen carbonate (4.6 g, 55 mmol) in dimethylformamide (100 mL), and the resulting mixture was stirred at 100° C. for 48 hours and then at 140°–145° C. for 6 hours. The mixture was concentrated in vacuo, and the residue was partitioned between ethyl acetate (250 mL) and water (100 mL). The organic layer was taken, dried over magnesium sulfate and concentrated. The residue was purified through a flash chromatography column on silica gel eluting with hexane/ethyl acetate (5:1) to afford compound C (9.2 g, 55%) as a solid.

Melting point: 107°–108° C.

D. 2-Butyl-4-hydro-3-oxo-6-(2,2,2-trifluoroethoxy)-5-quinoxalinecarboxylic acid, ethyl ester A mixture of compound C (8.5 g, 23 mmol) and manganese dioxide (12.0 g, 0.14 mol) in tetrahydrofuran (100 mL) was stirred at reflux temperature for 8 hours. The mixture was cooled to room temperature and filtered through a Celite® pad, washed with ethyl acetate, and the combined filtrate was concentrated and the residue was purified by a flash chromatography column on silica gel eluting with methylene chloride/ethyl acetate (10:1) to afford compound D (7.8 g, 92%) as a solid.

Melting point: 148.5°–149.5° C.

E. 2-Butyl-4-hydro-3-oxo-6-(2,2,2-trifluoroethoxy)-5-quinoxalinecarboxylic acid

A mixture of compound D (4.0 g, 10.8 mmol), powdered sodium hydroxide (2.59 g, 64.6 mmol) and 1,4,7,10,13,16-hexaoxacyclooctadecane ether (300 mg, 1.14 mmol) in toluene (60 mL) was stirred vigorously at reflux temperature for 4 hours. The reaction mixture was then cooled to room temperature and the product was extracted with water (3×30 mL). The extracted aqueous solution was acidified to pH 2 with 4N aqueous hydrochloric acid to precipitate compound E, which was collected, washed with water and dried (3.2 g, 86%).

Melting point: 221°–222° C.

F. 2-Butyl-3-chloro-6-(2,2,2-trifluoroethoxy)-5-quinoxalinecarboxylic acid

A suspension of compound E (3.2 g, 9.3 mmol) in phosphorus oxychloride (40 mL) was stirred at reflux temperature. It soon became a homogeneous solution and the solution was refluxed for 2 hours. Most of the excess phosphorus oxychloride was removed under reduced pressure. The residue (about 150 g) was poured onto ice. The mixture was extracted with ethyl acetate (2×50 mL), dried over sodium sulfate and concentrated. The residue was purified through a flash chromatography column on silica gel eluting with hexane/ethyl acetate/acetic acid (2:1:0.01) to afford compound F (1.05 g, 31%) as a solid, melting point 149°-150° C. and the associated diquinoxaline linked through the carboxyl (2.2 g), melting point 96°-97° C. The latter compound can be hydrolyzed into compound F quantitatively by treatment with 1N aqueous sodium hydroxide solution in tetrahydrofuran at room temperature.

$^1$H NMR (CDCl$_3$+DMSO-d$_6$) δ8.07 (d, J=9.4 Hz, 1H), 7.67 (d, J=9.4 Hz, 1H), 4.73 (q, J=8.2 Hz, 2H), 3.09 (t, J=7.6 Hz, 2H), 1.83 (qn, J=7.6 Hz, 2H), 1.48 (sx, J=7.6 Hz, 2H), 0.99 (t, J=7.6 Hz, 3H).

$^{13}$C NMR (CDCl$_3$+DMSO-d$_6$) δ166.3, 154.9, 153.5, 148.8, 138.1, 136.6, 130.6, 123.2 (q, J=277.8 Hz), 121.7, 118.6, 67.1 (q, J=35.2 Hz), 35.1, 29.4, 22.3, 13.9.

G. 2-Butyl-6-(2,2,2-trifluoroethoxy)-3-[[2'-(1H-tetrazol-5-yl)[1,1'-biphenyl]-4-yl]oxy]quinoxaline-5-carboxylic acid A mixture of compound F (0.95 g, 2.63 mmol), biphenyl B from Example 2 (0.66 g, 2.76 mmol) and cesium carbonate (2.70 g, 8.3 mmol) in dimethylformamide (10 mL) was stirred at 70° C. overnight. The mixture was cooled to room temperature and diluted with ethyl acetate (100 mL). Water (50 mL) was added to the mixture and the solution was adjusted to pH 3 with 2N aqueous hydrochloric acid. The organic solution was taken, washed with brine, dried over sodium sulfate and concentrated. The residue was triturated with ethyl ether to afford Example 26 (1.46 g, 98%) as a solid.

Melting point: 167°-168° C.

$^1$H NMR (DMSO-d$_6$) δ13.0 (br s, 1H), 8.08 (d, J=9.4 Hz, 1H), 7.63 (m, 5H), 7.38 (d, J=8.8 Hz, 2H), 7.17 (d, J=8.8 Hz, 2H), 5.00 (q, J=7.6 Hz, 2H), 3.06 (t, J=7.6 Hz, 2H), 1.83 (qn, J=7.6 Hz, 2H), 1.45 (sx, J=7.6 Hz, 2H), 0.96 (t, J=7.6 Hz, 3H).

$^{13}$C NMR (DMSO-d$_6$) δ166.2, 162.6, 155.2, 153.2, 152.3, 150.3, 141.0, 136.3, 136.2, 134.7, 131.5, 131.0, 130.1, 129.9, 128.1, 124.0 (q, J=277.3 Hz), 123.4, 121.0, 120.7, 115.6, 66.0 (q, J=34.6 Hz), 32.7, 29.1, 22.3, 14.1.

EXAMPLE 27

2-Butyl-6-(2,2,2-trifluoroethoxy)-3-[[2'-(1H-tetrazol-5-yl)[1,1'-biphenyl]-4-yl]oxy]quinoxaline-5-carboxylic acid, 1-oxide A mixture of Example 26 (282 mg, 0.5 mmol) and m-chloroperoxybenzoic acid (533 mg, 80-85% content) in methylene chloride (10 mL) was stirred at room temperature for 36 hours. The mixture was concentrated and the residue was purified by a flash chromatography column on silica gel eluting with hexane/ethyl acetate/acetic acid (1:1:0.01) to afford Example 27 (150 mg, 52%) as a solid.

Melting point: 172°-174° C. R$_f$=0.31 in ethyl acetate containing 1% acetic acid, silica gel plate. R$_t$=4.59 minutes at 254 nm, solvent system 78% aqueous methanol containing 0.2% phosphoric acid, 1.5% mL/min flow rate in YMC S3-ODS column (6.0×150 mm).

$^1$H NMR (CD$_3$OD) δ8.30 (d, J=9.4 Hz, 1H), 7.67 (m, 4H), 7.49 (d, J=9.4 Hz, 1H), 7.30 (d, J=8.8 Hz, 2H), 7.17 (d, J=8.8 Hz, 2H), 4.76 (q, J=7.8 Hz, 2H), 3.18 (t, J=7.6 Hz, 2H), 1.74 (qn, J=7.6 Hz, 2H), 1.58 (sx, J=7.6 Hz, 2H), 0.99 (t, J=7.6 Hz, 3H).

$^{13}$C NMR (CD$_3$OD) δ167.9, 159.6, 156.5, 153.6, 142.6, 138.8, 138.2, 137.8, 132.5, 131.9, 131.6, 131.1, 129.0, 125.0 (q, J=277.3 Hz), 124.3, 122.5, 122.1, 115.9, 67.6 (q, J=35.1 Hz), 28.3, 25.5, 23.9, 14.2.; MS (FAB) 581 (M+H)$^+$.

Analysis for C$_{28}$H$_{23}$F$_3$N$_6$O$_5$·0.24 H$_2$O: Calc'd: C, 57.51; H, 4.05; N, 14.37; F: 9.75; Found: C, 57.71; H, 3.79; N, 14.17; F: 10.10.

EXAMPLE 28

2-Butyl-6-(2,2,2-trifluoroethoxy)-3-[[2'-(1H-tetrazol-5-yl)[1,1'-biphenyl]-4-yl]oxy]quinoxaline-5-carboxylic acid, 2-methyl-1-(1-oxopropoxy)propyl ester A mixture of Example 26 (1.0 g, 1.78 mmol) and silver oxide (2.5 g, 10.8 mmol) in tetrahydrofuran (10 mL) was stirred in the presence of molecular sieves (2.5 g, 4 Å powder) at 65° C. for 5 minutes. To this mixture was added compound A from Example 18 (0.4 mL) and it was stirred at 65° C. overnight. The mixture was then cooled to 0° C., acidified with 2N aqueous hydrochloric acid (about 10 mL) and filtered through a Celite® pad. The pad was rinsed thoroughly with tetrahydrofuran. The combined filtrate was washed with brine, dried over sodium sulfate and concentrated. The residue was chromatographed on silica gel eluting with hexane/ethyl acetate/acetic acid (2:1:0.05) to afford Example 28 (0.4 g) as an oil and a dialkylated compound (0.95 g). The dialkylated compound was dissolved in methanol (10 mL) and stirred with saturated aqueous sodium hydrogen carbonate solution (3 mL) at 55° C. for 4 hours. Most of the methanol was removed under reduced pressure. The residue was acidified with 2N aqueous hydrochloric acid to pH 4 and partitioned between ethyl acetate (20 mL) and brine. The organic layer was taken, dried over sodium sulfate and concentrated in vacuo. The residue was chromatographed on silica gel eluting with hexane/ethyl acetate/acetic acid (2:1:0.01) to afford Example 28 (0.4 g, 80% overall) as an oil and the dialkylated compound both as carboxylic acid and tetrazole (0.27 g).

$^1$H NMR (CDCl$_3$) δ8.05 (d, J=8.8 Hz, 1H), 7.97 (d, J=7.0 Hz, 1H), 7.77-7.47 (m, 3H), 7.28 (d, J=9.4 Hz, 1H), 7.19 (s, 4H), 6.92 (d, J=5.3 Hz, 1H), 4.54 (q, J=8.2 Hz, 2H), 3.09 (t, J=7.6 Hz, 2H), 2.32 (q, J=7.6 Hz, 2H), 2.03 (ot, J=5.1 Hz, 1H), 1.86 (qn, J=7.6 Hz, 2H), 1.50 (sx, J=7.6 Hz, 2H), 1.04-0.89 (m, 12H).

$^{13}$C NMR (CDCl$_3$) δ173.4, 163.4, 156.1, 153.9, 152.3, 150.9, 140.5, 137.4, 136.2, 134.9, 131.1, 131.0, 130.7, 130.2, 130.0, 127.9, 121.7, 120.5 (q, J=277.3 Hz), 118.8, 114.2, 93.5, 67.1 (q, J=34:6 Hz), 33.1, 31.5, 29.6, 27.4, 22.6, 16.4, 15.9, 13.8, 8.7.

EXAMPLE 29

2-Butyl-6-(2,2,2-trifluoroethoxy)-3-[[2'-(1H-tetrazol-5-yl)[1,1'-biphenyl]-4-yl]oxy]quinoxaline-5-carboxylic acid, 2-methyl-1-(1-oxopropoxy)propyl ester, 1-oxide A mixture of Example 28 (0.78 g, 1.13 mmol) and m-chloroperoxybenzoic acid (1.0 g, 80-85% content) in methylene chloride (10 mL) was stirred at room temperature for 4 hours. The reaction mixture was directly loaded on a flash chromatography column on silica gel eluting with hexane/ethyl acetate/acetic acid (200:100:0.5) to afford Example 29 (0.65 g, 81%), which was dissolved in methanol and water to lyophilyze to obtain a white solid product.

Melting point: 92°-94° C. R$_f$=0.25 in 1% acetic acid in hexane-ethyl acetate (50/50), silica gel plate. R$_t$=8.43 minutes at 254 nm, solvent system 82% aqueous methanol containing 0.2% phosphoric acid, 1.5% mL/min flow rate in YMC S3-ODS column (6.0×150 mm).

$^1$H NMR (CDCl$_3$) δ8.49 (d, J=9.3 Hz, 1H), 7.93 (d, J=7.6 Hz, 1H), 7.63–7.48 (m, 3H), 7.27 (d, J=9.4 Hz, 1H), 7.19 (s, 4H), 6.88 (d, J=4.7 Hz, 1H), 4.58 (q, J=8.2 Hz, 2H), 3.21 (t, J=7.6 Hz, 2H), 2.32 (q, J=7.6 Hz, 2H), 2.00 (ot, J=5.9 Hz, 1H), 1.75 (qn, J=7.6 Hz, 2H), 1.50 (sx, J=7.6 Hz, 2H), 1.06 (t, J=7.6 Hz, 3H), 0.99 (t, J=7.0 Hz, 3H), 0.87 (t, J=7.6 Hz, 3H).

$^{13}$C NMR (CDCl$_3$) δ173.3, 162.6, 158.7, 155.2, 152.0, 140.5, 138.2, 136.8, 136.4, 131.0, 130.9, 130.8, 130.4, 130,0, 127.9, 123.2,, 122.7 (q, J=277.7 Hz), 122.1, 121.7, 119.4, 113.7, 93.5, 66.7 (q, J=37.1 Hz), 31.5, 27.3, 24.5, 22.8, 16.3, 15.8, 13.7, 8.6; MS 709 (M+H)$^+$, 693 (M+H−O)$^+$.

Analysis for C$_{35}$H$_{35}$F$_3$N$_6$O$_7$·0.14 H$_2$O: Calc'd: C, 59.10; H, 5.00; N, 11.82; F, 8.01; Found: C, 64.87; H, 5.99; N, 12.42.

EXAMPLE 30

2-Butyl-6-ethoxy-3-[[2'-(1H-tetrazol-5-yl)][1,1'-biphenyl]-4-yl]oxy]-5-quinoxalinecarboxylic acid, (5-methyl-2-oxo-1,3-dioxol-4-yl)methyl ester A mixture of Example 15 (0.51 g, 1.0 mmol) and silver oxide (1.53 g, 6.6 mmol) in tetrahydrofuran (5 mL) and 4-(bromomethyl)-5-methyl-2-oxo-1,3-dioxole (212.3 mg, 1.1 mmol) was stirred in the presence of molecular sieves (1.0 g, 4 Å powder) at room temperature for 1 hour and at 65° C. overnight. More silver oxide (1.0 g, 4.3 mmol) and dioxole (212.3 mg, 1 mmol) were added, and the mixture was stirred at 60° C. for an additional 3 hours. It was cooled to 0° C. and 12 mL of 2N aqueous hydrochloric acid was added. The mixture was filtered through a Celite ® pad and the pad was washed with tetrahydrofuran (50 mL). The filtrate solution was washed with brine, dried over sodium sulfate and concentrated. The residue was chromatographed on silica gel eluting with hexane/ethyl acetate/acetic acid (2:1:0.01) to yield Example 30 (0.31 g, 50%) as an oil.

$^1$H NMR (CDCl$_3$) δ8.00 (d, J=9.4 Hz, 1H), 7.83 (d, J=7.0 Hz, 1H), 7.59–7.43 (m, 3H), 7.34–7.17 (m, 5H), 4.97 (d, J=4.1 Hz, 1H), 4.68 (d, J=4.1 Hz, 1H), 4.20 (m, 2H), 3.06 (t, J=7.6 Hz, 2H), 1.81 (m, 5H), 1.55–1.37 (m, 5H), 0.98 (t, J=7.6 Hz, 3H).

EXAMPLE 31

2-Butyl-6-ethoxy-3-[[2'-(1H-tetrazol-5-yl)][1,1'-biphenyl]-4-yl]oxy]-5-quinoxalinecarboxylic acid, (5-methyl-2-oxo-1,3-dioxol-4-yl)methyl ester, 1-oxide A mixture of Example 30 (0.3 g, 0.48 mmol) and m-chloroperoxybenzoic acid (98 mg, 80–85% content) in methylene chloride (2 mL) was stirred at room temperature overnight. More m-chloroperoxybenzoic acid (50 mg) was added and the mixture was stirred at room temperature for 2 hours more. The reaction mixture was loaded on a flash chromatography column on silica gel and eluted with hexane/ethyl acetate/acetic acid (1:1:0.01). The desired fractions were pooled and concentrated under reduced pressure. The residue was repurified by preparative HPLC (column: YMC S-10 ODS 3×500 mm; flow rate: 30 mL/min; solvent system: 78% methanol containing 0.1% trifluoroacetic acid; UV 254 nm) to yield Example 31 (98.5 mg, 32%) as a solid.

Melting point: 233°–234° C. R$_f$=0.27 in 1% acetic acid in hexane-ethyl acetate (50/50), silica gel plate. R$_t$=6.19 minutes at 254 nm, solvent system of 78% aqueous methanol containing 0.2% phosphoric acid, 1.5% mL/min flow rate in YMC S3-ODS column (6.0×150 mm).

$^1$H NMR (CDCl$_3$) δ8.56 (d, J=9.4 Hz, 1H), 7.91 (dd, J=1.2, 7.1 Hz, 1H), 7.65–7.50 (m, 3H), 7.33–7.25 (m, 5H), 5.03 (d, J=4.7 Hz, 1H), 4.72 (d, J=4.7 Hz, 1H), 4.24 (m, 2H), 3.22 (t, J=7.6 Hz, 2H), 1.85 (s, 3H), 1.75 (qn, J=7.6 Hz, 2H), 1.50 (sx, J=7.6 Hz, 2H), 1.45 (t, J=7.0 Hz, 3H), 0.98 (t, J=7.6 Hz, 3H);

$^{13}$C NMR (CDCl$_3$) δ162.7, 158.1, 157.9, 154.6, 152.7, 151.8, 140.8, 138.5, 136.2, 131.3, 130.9, 130.1, 129.5, 128.0, 122,7, 122.6, 121.6, 113.3, 102.8, 90.0, 65.2, 27.5, 25.2, 24.5, 22.9, 14.8, 13.8; MS 639 (M+H)$^+$, 623 (M+H−O)$^+$.

Analysis for C$_{33}$H$_{30}$N$_6$O$_8$·H$_2$O: Calc'd: C, 61.67; H, 4.87; N, 13.07; Found: C, 61.71; H, 4.74; N, 13.03.

EXAMPLE 32

2-Butyl-6-(butyloxy)-3-[[2'-(2H-tetrazol-5-yl)-[1,1'-biphenyl]-4-yl]oxy]-5-quinoxalinecarboxylic acid, 2-methyl-1-(1-oxopropoxy)propyl ester A mixture of Example 24 (0.51 g, 0.95 mmol) and silver oxide (1.50 g, 6.5 mmol) in tetrahydrofuran (5 mL) was stirred in the presence of molecular sieves (1.5 g, 4 Å powder) at 65° C. for 5 minutes. Propanoic acid, 1-chloro-2-methylpropyl ester (0.4 mL) was then added and the resulting mixture was stirred at 65° C. for 4 hours. It was cooled to 0° C., acidified with 1N aqueous hydrochloric acid (15 mL) and filtered through a Celite ® pad, and the pad was washed with tetrahydrofuran (50 mL). The combined filtrate solution was washed with brine, dried over sodium sulfate and concentrated. The crude product, which contained a dialkylated analogue, was dissolved in methanol (10 mL) and 5% aqueous sodium hydrogen carbonate (2.0 mL), and the mixture was stirred at room temperature for 1 hour. Solid sodium hydrogen carbonate (0.5 g) was added and the mixture was stirred at room temperature for 5 hours more. It was acidified with 1N aqueous hydrochloric acid and concentrated. The residue was partitioned between ethyl acetate (20 mL) and water (20 mL). The organic layer was separated, washed with brine, dried over sodium sulfate and concentrated. The residue was chromatographed on silica gel eluting with hexane/ethyl acetate/acetic acid (2:1:0.01) to afford Example 32 (0.36 g, 57%) as an oil and the dialkylated compound (0.41 g), contaminated with small amount of impurities.

$^1$H NMR (CDCl$_3$) δ7.97 (d, J=9.4 Hz, 1H), 7.95 (d, J=7.0 Hz, 1H), 7.59–7.46 (m, 3H), 7.30 (d, J=9.4 Hz, 1H), 7.17 (m, 4H), 6.92 (d, J=5.3 Hz, 1H), 4.15 (m, 2H), 3.06 (t, J=7.6 Hz, 2H), 2.30 (q, J=7.0 Hz, 2H), 2.02 (ot, J=5.1 Hz, 1H), 1.81 (m, 4H), 1.51 (m, 4H), 1.07–0.88 (m, 15H);

$^{13}$C NMR (CDCl$_3$) δ173.1, 164.3, 156.1, 155.7, 152.4, 149.3, 140.6, 135.8, 133.9, 130.9, 130.8, 130.6, 130.5, 129.9, 127.8, 123.0, 121.6, 116.9, 114.0, 93.3, 69.1, 33.0, 31.5, 31.1, 29.7, 27.3, 22.5, 18.9, 16.4, 15.9, 13.8, 13.6, 8.7.

EXAMPLE 33

2-Butyl-6-(butyloxy)-3-[[2'-(2H-tetrazol-5-yl)[1,1'-biphenyl]-4-yl]oxy]-5-quinoxalinecarboxylic acid, 2-methyl-1-(1-oxopropoxy)propyl ester, 1-oxide A mixture of Example 32 (0.36 g, 0.54 mmol) and m-chloroperoxybenzoic acid (0.56 g, 80–85% content) in methylene chloride (3 mL) was stirred at room temperature for 3 hours. The solid was filtered and the filtrate solution was passed through a flash chromatography column on silica gel eluting with hexane/ethyl acetate/acetic acid (2:1:0.01) to afford Example 33 (0.21 g, 57%), which was dissolved in methanol and water to lyophilyze to obtain a white solid product.

Melting point: 75°–78° C. $R_f$=0.46 in 1% acetic acid in hexane-ethyl acetate (50/50), silica gel plate. $R_t$=8.69 minutes at 254 nm, solvent system 86% aqueous methanol containing 0.2% phosphoric acid, 1.5% mL/min flow rate in YMC S3-ODS column (6.0×150 mm).

$^1$H NMR (CDCl$_3$) δ8.47 (d, J=9.4 Hz, 1H), 7.90 (d, J=7.6 Hz, 1H), 7.60–7.31 (m, 3H), 7.28 (d, J=9.4 Hz, 1H), 7.17 (s, 4H), 6.88 (d, J=4.7 Hz, 1H), 4.17 (t, J=6.4 Hz, 2H), 3.19 (t, J=7.6 Hz, 2H), 2.32 (q, J=7.6 Hz, 2H), 2.00 (ot, J=5.3 Hz, 1H), 1.65 (m, 4H), 1.56 (m, 4H), 1.09–0.85 (m, 15H);

$^{13}$C NMR (CDCl$_3$) δ172.8, 163.5, 158.1, 157.5, 152.0, 140.4, 138.0, 136.1, 135.7, 130.9, 130.7, 130.6, 129.9, 129.0, 128.8, 128.0, 123.0, 121.4, 117.8, 113.7, 93.4, 69.2, 31.4, 30.9, 27.2, 24.4, 22.7, 18.8, 16.3, 15.8, 13.7, 13.5, 8.7; MS 683 (M+H)$^+$, 667 (M+H–O)$^+$.

Analysis for C$_{37}$H$_{42}$N$_6$O$_7$: Calc'd: C, 64.78; H, 6.22; N, 12.25; Found: C, 64.78; H, 6.19; N, 12.15.

What is claimed is:

1. A compound of formula

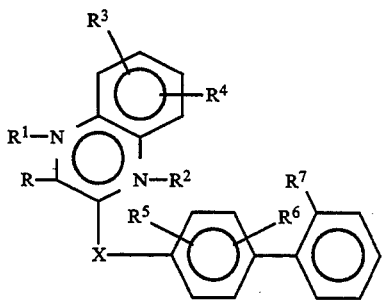

or a pharmaceutically acceptable salt thereof, wherein:
X is —O— or —CH$_2$—;
R is hydrogen, alkyl, aryl, aralkyl, cycloalkyl, or cycloalkylalkyl;
R$^1$ and R$^2$ are each independently O or absent;
R$^3$ is hydrogen, alkyl, alkenyl, alkoxy, cycloalkyl, aryl, aralkyl, cycloalkylalkyl, —NR$^{17}$R$^{18}$, halo haloalkyl, or haloalkoxy;
R$^4$ is hydrogen, alkyl, alkenyl, alkoxy, aryl, cycloalkyl, aralkyl, cycloalkylalkyl, —R$^8$—OH, or —R$^8$-CO$_2$R$^9$;
R$^5$ and R$^6$ are each independently hydrogen, alkyl, alkoxy, halogen, or haloalkyl;

R$^7$ is —(CH$_2$)$_n$—CO$_2$R$^9$, $-\overset{R^{12}}{\underset{}{C}}O_2CH-O\overset{O}{\underset{}{C}}-R^{13}$, —NHSO$_2$haloalkyl, $-O-\overset{O}{\underset{OH}{\overset{\|}{S}}}-OH$, —SO$_3$H, —C(haloalkyl)$_2$OH, $-O-\overset{O}{\underset{OH}{\overset{\|}{P}}}-OH$, —PO$_3$H$_2$, $NH\overset{O}{\underset{OH}{\overset{\|}{P}}}-OH$, —CONHOR$^{12}$, —CONHNHSO$_2$haloalkyl, —(CH$_2$)$_n$-5-tetrazolyl (optionally substituted with R$^9$),

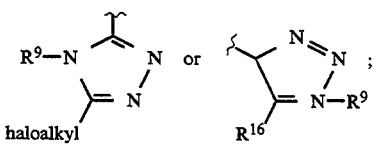

R$^8$ is a single bond, alkyl, alkenyl, aryl, or aralkyl;
R$^9$ is hydrogen, alkyl, cycloalkyl, aryl, aralkyl,

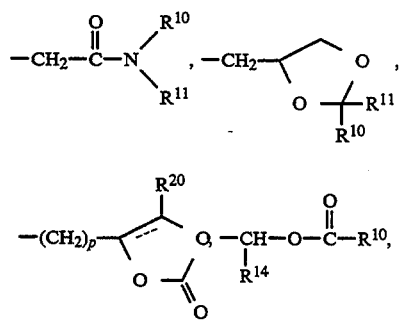

alkali metal, or ammonium;
R$^{10}$ and R$^{11}$ are each independently hydrogen, alkyl, alkoxy, cycloalkyl, aryl, or aralkyl, or R$^{10}$ and R$^{11}$ together are —(CH$_2$)$_2$—, —CH$_2$)$_3$—, —CH═CH—, or

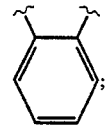

R$^{12}$ is hydrogen, alkyl, aryl, cycloalkyl, or aralkyl;
R$^{13}$ is alkyl, —NR$^{10}$R$^{11}$, or

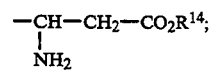

R$^{14}$ is hydrogen, alkyl, perfluoroalkyl, cycloalkyl, phenyl, or benzyl;
R$^{15}$ is hydrogen, alkyl, or phenyl;
R$^{16}$ is —CN, —NO$_2$, or —CO$_2$R$^{14}$;
R$^{17}$ and R$^{18}$ are each independently hydrogen, alkyl of 1 to 4 carbon atoms, phenyl, benzyl, a-methylbenzyl, or together with the nitrogen atom to which they are attached are

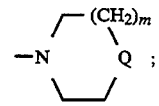

Q is —NR$^{19}$, —O—, or —CH$_2$—;
R$^{19}$ is hydrogen, alkyl, aryl, aralkyl, cycloalkyl, or cycloalkylalkyl;
R$^{20}$ is hydrogen, alkyl, aryl, cycloalkyl, aralkyl, or cycloalkylalkyl;
m is 0 or 1;
n is 0, 1, or 2; and
p is 1, 2, 3, or 4.

2. The compound of claim 1, wherein X is —O—.

3. The compound of claim 1, wherein R is alkyl of 1 to 4 carbon atoms.

4. The compound of claim 1, wherein $R^2$ is O.

5. The compound of claim 1, wherein $R^3$ is hydrogen, alkoxy or haloalkoxy.

6. The compound of claim 1, wherein $R^4$ is hydrogen or $-CO_2R^9$.

7. The compound of claim 1, wherein $R^5$ and $R^6$ are hydrogen.

8. The compound of claim 1, wherein $R^7$ is -5-tetrazolyl.

9. The compound of claim 1, wherein $R^4$ is $-CO_2R^9$ and $R^9$ is hydrogen, alkyl, alkali metal,

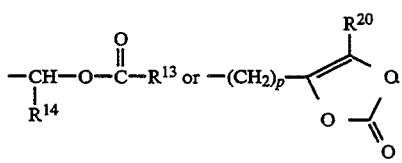

10. The compound of claim 9, wherein $R^{13}$, $R^{14}$ and $R^{20}$ are each independently alkyl.

11. The compound of claim 9, wherein p is 1.

12. The compound of claim 1, selected from the group consisting of:

2-Butyl-3-[[2'-(1H-tetrazol-5-yl)[1,1'-biphenyl]-4-yl]oxy]quinoxaline;

2-Butyl-3-[[2'-(1H-tetrazol-5-yl)[1,1'-biphenyl]-4-yl]oxy]quinoxaline, 4-oxide;

2-Butyl-3-[[2'-(1H-tetrazol-5-yl)[1,1'-biphenyl]-4-yl]oxy]-quinoxaline-5-carboxylic acid;

2-Butyl-3-[[2'-(1H-tetrazol-5-yl)[1,1'-biphenyl]-4-yl]oxy]-quinoxaline-5-carboxylic acid, methyl ester;

2-Butyl-3-[[2'-(1H-tetrazol-5-yl)[1,1'-biphenyl]-4-yl]oxy]-quinoxaline-5-carboxylic acid, ethyl ester;

2-Butyl-3-[[2'-(1H-tetrazol-5-yl)[1,1'-biphenyl]-4-yl]oxy]-quinoxaline-5-carboxylic acid, ethyl ester, 1-oxide;

2-Butyl-3-[[2'-(1H-tetrazol-5-yl)[1,1'-biphenyl]-4-yl]oxy]-quinoxaline-5-carboxylic acid, methyl ester 1-oxide;

2-Butyl-3-[[2'-(1H-tetrazol-5-yl)[1,1'-biphenyl]-4-yl]oxy]-quinoxaline-5-carboxylic acid, 1-oxide;

2-Butyl-3-[4-[2-(1H-tetrazol-5-yl)phenyl]phenylmethyl]quinoxaline, sodium salt;

2-Butyl-3-[4-[2-(1H-tetrazol-5-yl)phenyl]phenylmethyl]quinoxaline, 4-oxide;

2-Butyl-3-[4-[2-(1H-tetrazol-5-yl)phenyl]phenylmethyl]quinoxaline, 1-oxide;

2-Butyl-3-[4-[2-(1H-tetrazol-5-yl)phenyl]phenylmethyl]quinoxaline, 1,4-dioxide;

2-Butyl-6-ethoxy-3-[[2'-(1H-tetrazol-5-yl)[1,1'-biphenyl]-4-yl]oxy]quinoxaline-5-carboxylic acid, methyl ester;

2-Butyl-6-ethoxy-3-[[2'-(1H-tetrazol-5-yl)[1,1'-biphenyl]-4-yl]oxy]quinoxaline-5-carboxylic acid, methyl ester, 1-oxide;

2-Butyl-6-ethoxy-3-[[2'-(1H-tetrazol-5-yl)[1,1'-biphenyl]-4-yl]oxy]quinoxaline-5-carboxylic acid;

2-Butyl-6-ethoxy-3-[[2'-(1H-tetrazol-5-yl)[1,1'-biphenyl]-4-yl]oxy]quinoxaline-5-carboxylic acid, 1-oxide;

2-Butyl-3-[2'-(2H-tetrazol-5-yl)[1,1'-biphenyl]-4-yloxy]-5-quinoxolinecarboxylic acid, 2-methyl-1-(1-oxopropoxy)propyl ester, 1-oxide, monosodium salt;

2-Butyl-6-ethoxy-3-[[2'-(1H-tetrazol-5-yl)[1,1'-biphenyl]-4-yl]oxy]quinoxaline-5-carboxylic acid, 2-methyl-1-(1-oxopropoxy)propyl ester;

2-Butyl-6-ethoxy-3-[[2'-(1H-tetrazol-5-yl)[1,1'-biphenyl]-4-yl]oxy]quinoxaline-5-carboxylic acid, 2-methyl-1-(1-oxopropoxy)propyl ester, 1-oxide;

2-Butyl-6-(1-methylethoxy)-3-[[2'-(1H-tetrazol-5-yl)[1,1'-biphenyl]-4-yl]oxy]quinoxaline-5-carboxylic acid;

2-Butyl-6-(1-methylethoxy)-3-[[2'-(1H-tetrazol-5-yl)[1,1'-biphenyl]-4-yl]oxy]quinoxaline-5-carboxylic acid, 1-oxide;

2-Butyl-6-(1-methylethoxy)-3-[[2'-(1H-tetrazol-5-yl)[1,1'-biphenyl]-4-yl]oxy]quinoxaline-5-carboxylic acid, 2-methyl-1-(1-oxopropoxy)propyl ester;

2-Butyl-6-(1-methylethoxy)-3-[[2'-(1H-tetrazol-5-yl)[1,1'-biphenyl]-4-yl]oxy]quinoxaline-5-carboxylic acid, 2-methyl-1-(1-oxopropoxy)propyl ester, 1-oxide;

2-Butyl-6-butoxy-3-[[2'-(1H-tetrazol-5-yl)[1,1'-biphenyl]-4-yl]oxy]quinoxaline-5-carboxylic acid;

2-Butyl-6-butoxy-3-[[2'-(1H-tetrazol-5-yl)[1,1'-biphenyl]-4-yl]oxy]quinoxaline-5-carboxylic acid, 1-oxide;

2-Butyl-6-(2,2,2-trifluoroethoxy)-3-[[2'-(1H-tetrazol-5-yl)[1,1'-biphenyl]-4-yl]oxy]quinoxaline-5-carboxylic acid;

2-Butyl-6-(2,2,2-trifluoroethoxy)-3-[[2'-(1H-tetrazol-5-yl)[1,1'-biphenyl]-4-yl]oxy]quinoxaline-5-carboxylic acid, 1-oxide;

2-Butyl-6-(2,2,2-trifluoroethoxy)-3-[[2'-(1H-tetrazol-5-yl)[1,1'-biphenyl]-4-yl]oxy]quinoxaline-5-carboxylic acid, 2-methyl-1-(1-oxopropoxy)propyl ester;

2-Butyl-6-(2,2,2-trifluoroethoxy)-3-[[2'-(1H-tetrazol-5-yl)[1,1'-biphenyl]-4-yl]oxy]quinoxaline-5-carboxylic acid, 1-oxide, 2-methyl-1-(1-oxopropoxy)propyl ester;

2-Butyl-6-ethoxy-3-[[2'-(1H-tetrazol-5-yl)[[1,1'-biphenyl]-4-yl]oxy]-5-quinoxalinecarboxylic acid, (5-methyl-2-oxo-1,3-dioxol-4-yl)methyl ester;

2-Butyl-6-ethoxy-3-[[2'-(1H-tetrazol-5-yl)[[1,1'-biphenyl]-4-yl]oxy]-5-quinoxalinecarboxylic acid, (5-methyl-2-oxo-1,3-dioxol-4-yl)methyl ester, 1-oxide;

2-Butyl-6-(butyloxy)-3-[[2'-(2H-tetrazol-5-yl)-[1,1'-biphenyl]-4-yl]oxy]-5-quinoxalinecarboxylic acid, 2-methyl-1-(1-oxopropoxy)propyl ester; and 2-Butyl-6-(butyloxy)-3-[[2'-(2H-tetrazol-5-yl)[1,1'-biphenyl]-4-yl]oxy]-5-quinoxalinecarboxylic acid, 2-methyl-1-(1-oxopropoxy)propyl ester, 1-oxide.

13. A method of treating hypertension comprising administering to a mammal in need thereof a therapeutically effective amount of a compound of claim 1.

14. A method of treating congestive heart failure comprising administering to a mammal in need thereof a therapeutically effective amount of a compound of claim 1.

15. A method of preventing cardiac hypertrophy comprising administering to a mammal in need thereof a therapeutically effective amount of a compound of claim 1.

* * * * *